US010588939B2

(12) United States Patent
Aguilar et al.

(10) Patent No.: US 10,588,939 B2
(45) Date of Patent: Mar. 17, 2020

(54) METHOD OF TREATING A BLADDER CANCER USING A CHIMERIC EGF-TARGETED BACTERIAL TOXIN

(71) Applicant: Purdue Research Foundation, West Lafayette, IN (US)

(72) Inventors: Ruben Claudio Aguilar, West Lafayette, IN (US); Timothy L. Ratliff, West Lafayette, IN (US)

(73) Assignee: Purdue Research Foundation/OTC, West Lafayette, IN (US)

( * ) Notice: Subject to any disclaimer, the term of this patent is extended or adjusted under 35 U.S.C. 154(b) by 0 days.

(21) Appl. No.: 15/590,225

(22) Filed: May 9, 2017

(65) Prior Publication Data

US 2017/0319657 A1 Nov. 9, 2017

Related U.S. Application Data

(60) Provisional application No. 62/333,438, filed on May 9, 2016.

(51) Int. Cl.
*A61K 38/18* (2006.01)
*A61K 38/16* (2006.01)
(Continued)

(52) U.S. Cl.
CPC ........ *A61K 38/1808* (2013.01); *A61K 38/164* (2013.01); *A61K 47/6415* (2017.08);
(Continued)

(58) Field of Classification Search
CPC ........ A61K 39/09; A61K 38/19; A61K 39/02; A61K 39/07; A61K 39/08; A61K 39/10; A61K 39/108; A61K 39/40; A61K 47/48; A61K 38/00; A61P 3/00; A61P 3/10; A61P 5/14; A61P 19/04; A61P 21/04;
(Continued)

(56) References Cited

U.S. PATENT DOCUMENTS

2011/0280908 A1* 11/2011 Leppla ............ A61K 47/48353 424/237.1
2016/0362458 A9 12/2016 Mechaly et al.

FOREIGN PATENT DOCUMENTS

WO WO 2013/126690 * 8/2013 ............ C07K 19/00

OTHER PUBLICATIONS

Carlsson et al., (Radiol Oncol. 2015; 49(1):50-58. Available online Mar. 3, 2015).*

(Continued)

*Primary Examiner* — Jana A Hines
(74) *Attorney, Agent, or Firm* — Thomas|Horstemeyer, LLP

(57) ABSTRACT

Provided is a method of treating a bladder cancer in an animal or human comprising: administering to an animal or human patient a therapeutic composition comprising a first fusion protein capable of specifically binding to an epidermal growth factor receptor (EGFR) on the surface of a cancer cell and comprising an epidermal growth factor (EGF) polypeptide conjugated to a bacterial toxin polypeptide and a second fusion protein comprising an anthrax Lethal Factor N-terminus ($LF_N$) conjugated to a Diptheria Toxin A (DTA) catalytic domain.

1 Claim, 12 Drawing Sheets

Specification includes a Sequence Listing.

(51) Int. Cl.
*C07K 14/34* (2006.01)
*C07K 14/32* (2006.01)
*C07K 14/485* (2006.01)
*A61K 47/64* (2017.01)

(52) U.S. Cl.
CPC .............. *C07K 14/32* (2013.01); *C07K 14/34* (2013.01); *C07K 14/485* (2013.01); *C07K 2319/00* (2013.01); *C07K 2319/55* (2013.01)

(58) Field of Classification Search
CPC .......... A61P 29/00; A61P 31/12; A61P 31/14; A61P 31/18; A61P 31/20; A61P 31/22; A61P 35/00; A61P 35/02; A61P 37/00; C07H 21/04; C07K 14/195; C07K 14/32; C07K 16/30
USPC ......... 424/236.1, 237.1, 239.1, 240.1, 241.1; 536/23.1
See application file for complete search history.

(56) References Cited

OTHER PUBLICATIONS

Abbo et al., "Phase I Clinical Trial and Pharmacokinetics of Intravesical Mitomycin C in Dogs with Localized Transitional Cell Carcinoma of the Urinary Bladder," J. Vet. Intern. Med., 2010, vol. 24, pp. 1124-1130.
Bryant et al., "EGF induces macropinocytosis and SNX1-modulated recycling of E-cadherin," J. of Cell Science, Apr. 2007, vol. 120, pp. 1818-1828.
Burke et al., "Regulation of Epidermal Growth Factor Receptor Signaling by Endocytosis and Intracellular Trafficking," Molecular Biology of the Cell, Jun. 2001, vol. 12, pp. 1897-1910.
Chun et al., "Phase II Clinical Trial of Carboplatin in Canine Transitional Cell Carcinoma of the Urinary Bladder," J. Vet. Intern. Med. Sep.-Oct. 1997, vol. 11, No. 5, pp. 279-283.
Coon et al., "Fibronectin attachment protein from bacillus Calmette-Guerin as targeting agent for bladder tumor cells," Int. J. Cancer, 2012, vol. 131, pp. 591-600.
DeGraff et al., "When urothelial differentiation pathways go wrong: Implications for bladder cancer development and progression," Urologic Oncology: Seminars and Original Investigations, 2013, vol. 31, pp. 802-811.
Hendriks et al., "Coregulation of Epidermal Growth Factor Receptor/Human Epidermal Growth Factor Receptor 2 (HER2) Levels and Locations: Quantitative Analysis of HER2 Overexpression Effects," Cancer Research, Mar. 2003, vol. 63, pp. 1130-1137.
Mechaly et al., "Changing the Receptor Specificity of Anthrax Toxin," mBio, May 2012, vol. 3, No. 3, e00088-12.doi:10.1128/mBio.00088-12.
Messing, Edward M., "Clinical Implications of the Expression of Epidermal Growth Factor Receptors in Human Transitional Cell Carcinoma," Cancer Research, Apr. 1990, vol. 50, pp. 2530-2537.
Orth et al., "A Novel Endocytic Mechanism of Epidermal Growth Factor Receptor Sequestration and Internalization," Cancer Research, Apr. 2006, vol. 66, No. 7, pp. 3603-3610.
Redelman-Sidi et al., "Oncogenic Activation of Pak1-Dependent Pathway of Macropinocytosis Determines BCG Entry into Bladder Cancer Cells," Cancer Research, Feb. 2013, vol. 73, No. 3, pp. 1156-1167.
Romih et al., "Differentiation of epithelial cells in the urinary tract," Cell Tissue Research, 2005, vol. 320, pp. 259-268.
Roskoski Jr., Robert, "The ErbB/HER family of protein-tyrosine kinases and cancer," Pharmacological Research, 2014, vol. 79, pp. 34-74.
Shoop et al., "Anthrax lethal factor inhibition," PNAS, May 2005, vol. 102, No. 22, pp. 7958-7963.
Sinn et al., "The Wbronectin attachment protein of bacillus Calmette-Guerin (BCG) mediates antitumor activity," Cancer Immunol. Immunother., 2008, vol. 57, pp. 573-579.
Wang et al., "Oncolytic Viral Therapy by Bladder Instillation Using an E1A, E1B Double-Restricted Adenovirus in an Orthotopic Bladder Cancer Model," Urology, 2006, vol. 68, pp. 674-681.
Yeung et al., "The Health Economics of Bladder Cancer: An Updated Review of the Published Literature," PharmacoEconomics, 2014, vol. 32, pp. 1093-1104.
Young and Collier, "Anthrax Toxin: Receptor Binding, Internalization, Pore Formation, and Translocation." Annu. Rev. Biochem., 2007, vol. 76, pp. 243-265.
Zaharoff et al., "Intravesical Immunotherapy of Superficial Bladder Cancer with Chitosan/Interleukin-12," Cancer Research, Aug. 2009, vol. 69, No. 15, pp. 6192-6199.
Sommer, et al. (2018) Naturally-Occuring Canine Invasive Urothelial Carcinoma: A Model for Emerging Therapies. Bladder Cancer: 4: 149-159.

* cited by examiner

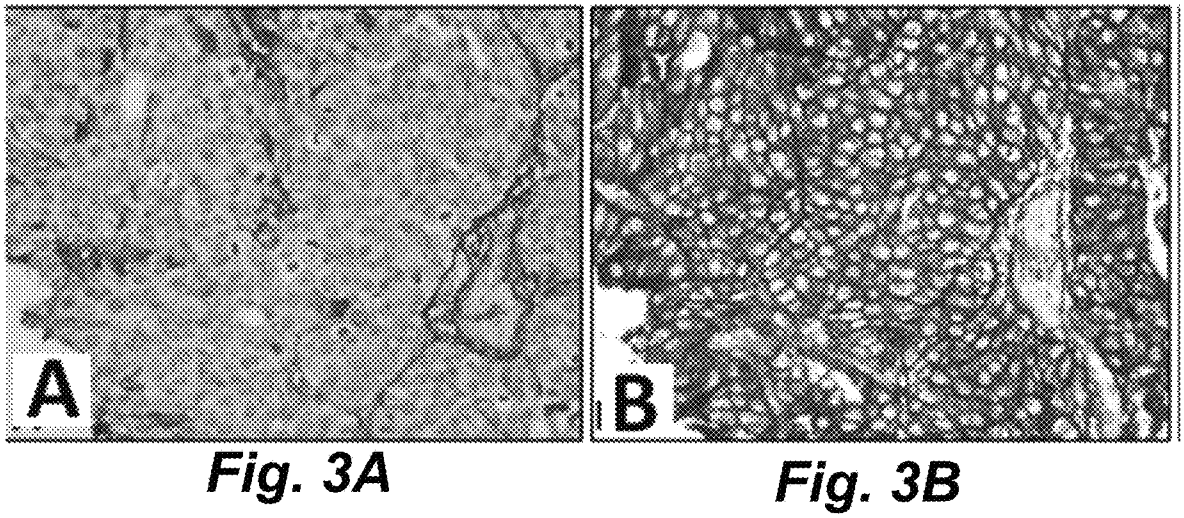
Fig. 3A
Fig. 3B
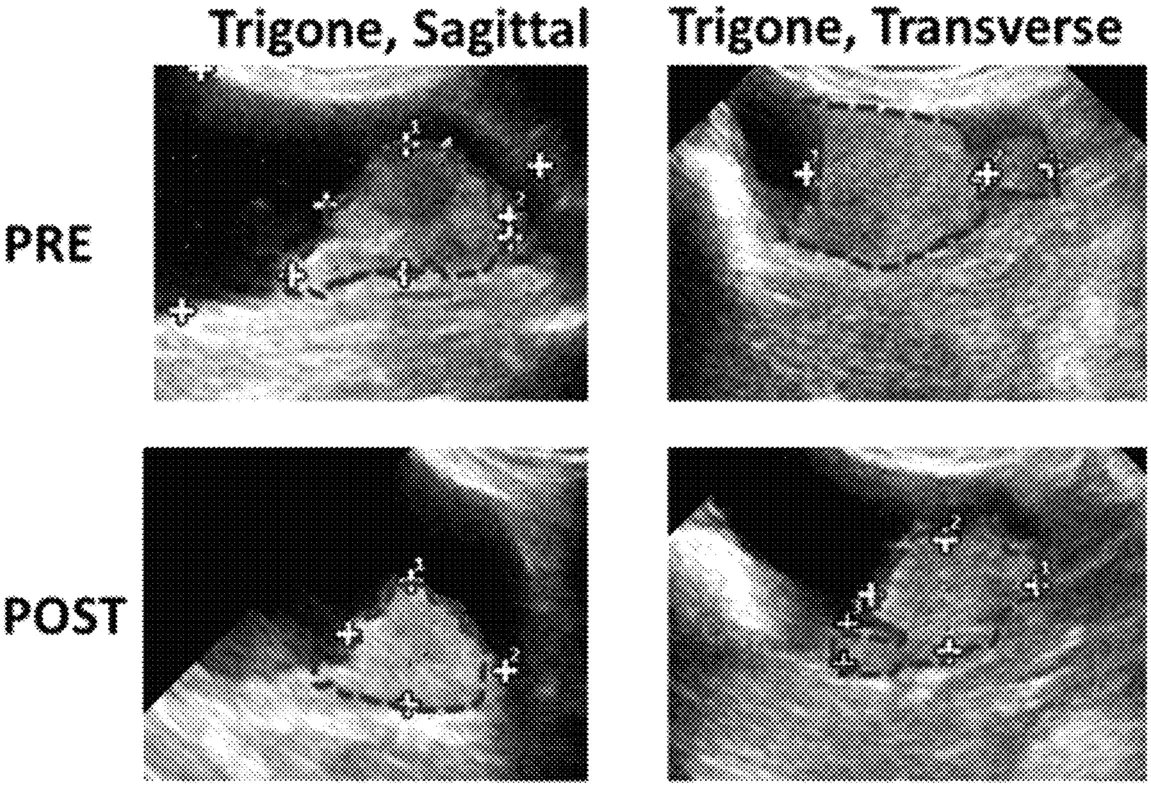
Fig. 3C

SEQUENCE LISTING

```
<160> NUMBER OF SEQ ID NOS: 10

<210> SEQ ID NO 1
<211> LENGTH: 8
<212> TYPE: PRT
<213> ORGANISM: Artificial sequence
<220> FEATURE:
<223> OTHER INFORMATION: Synthetic peptide

<400> SEQUENCE: 1

Ser Pro Gly His Lys Thr Gln Pro
1               5


<210> SEQ ID NO 2
<211> LENGTH: 27
<212> TYPE: DNA
<213> ORGANISM: Artificial sequence
<220> FEATURE:
```

-continued

<223> OTHER INFORMATION: Synthetic primer PAFor

<400> SEQUENCE: 2
gatttagtaa ttcgaattca agtacgg 27

<210> SEQ ID NO 3
<211> LENGTH: 32
<212> TYPE: DNA
<213> ORGANISM: Artificial sequence
<220> FEATURE:
<223> OTHER INFORMATION: Synthetic primer PARevEGF

<400> SEQUENCE: 3
cattcagagt cgctgtttgg ttgcgtttta tg 32

<210> SEQ ID NO 4
<211> LENGTH: 32
<212> TYPE: DNA
<213> ORGANISM: Artificial sequence
<220> FEATURE:
<223> OTHER INFORMATION: Synthetic primer PARevDTR

<400> SEQUENCE: 4
gttttatgcc ccggagatcc tatctcatag cc 32

<210> SEQ ID NO 5
<211> LENGTH: 32
<212> TYPE: DNA
<213> ORGANISM: Artificial sequence
<220> FEATURE:
<223> OTHER INFORMATION: Synthetic primer EGFFor

<400> SEQUENCE: 5
cataaaacgc aaccaaacag cgactatgaa tg 32

<210> SEQ ID NO 6
<211> LENGTH: 35
<212> TYPE: DNA
<213> ORGANISM: Artificial sequence
<220> FEATURE:
<223> OTHER INFORMATION: Sythetic primer EGFRev

<400> SEQUENCE: 6
ggtggtgctc gagtcaacgg agctcccacc atttc 35

<210> SEQ ID NO 7
<211> LENGTH: 32
<212> TYPE: DNA
<213> ORGANISM: Artificial sequence
<220> FEATURE:
<223> OTHER INFORMATION: Synthetic primer DTRFor

<400> SEQUENCE: 7
ggctatgaga taggatctcc ggggcataaa ac 32

<210> SEQ ID NO 8
<211> LENGTH: 36
<212> TYPE: DNA
<213> ORGANISM: Artificial sequence
<220> FEATURE:
<223> OTHER INFORMATION: Synthetic primer DTRRev

<400> SEQUENCE: 8
gtggtggtgg tggtgctcga gtcagctttt gatttc 36

```
<210> SEQ ID NO 9
<211> LENGTH: 764
<212> TYPE: PRT
<213> ORGANISM: Bacillus anthracis
<220> FEATURE:
<221> NAME/KEY: MISC_FEATURE
<223> OTHER INFORMATION: Anthrax Protective Antigen with 29 amino acid
      signal peptide

<400> SEQUENCE: 9

Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val Lys
            20                  25                  30

Gln Glu Asn Arg Leu Leu Asn Glu Ser Glu Ser Ser Ser Gln Gly Leu
        35                  40                  45

Leu Gly Tyr Tyr Phe Ser Asp Leu Asn Phe Gln Ala Pro Met Val Val
    50                  55                  60

Thr Ser Ser Thr Thr Gly Asp Leu Ser Ile Pro Ser Ser Glu Leu Glu
65                  70                  75                  80

Asn Ile Pro Ser Glu Asn Gln Tyr Phe Gln Ser Ala Ile Trp Ser Gly
                85                  90                  95

Phe Ile Lys Val Lys Lys Ser Asp Glu Tyr Thr Phe Ala Thr Ser Ala
            100                 105                 110

Asp Asn His Val Thr Met Trp Val Asp Asp Gln Glu Val Ile Asn Lys
        115                 120                 125

Ala Ser Asn Ser Asn Lys Ile Arg Leu Glu Lys Gly Arg Leu Tyr Gln
    130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
            180                 185                 190

Arg Lys Lys Arg Ser Thr Ser Ala Gly Pro Thr Val Pro Asp Arg Asp
        195                 200                 205

Asn Asp Gly Ile Pro Asp Ser Leu Glu Val Glu Gly Tyr Thr Val Asp
    210                 215                 220

Val Lys Asn Lys Arg Thr Phe Leu Ser Pro Trp Ile Ser Asn Ile His
225                 230                 235                 240

Glu Lys Lys Gly Leu Thr Lys Tyr Lys Ser Ser Pro Glu Lys Trp Ser
                245                 250                 255

Thr Ala Ser Asp Pro Tyr Ser Asp Phe Glu Lys Val Thr Gly Arg Ile
            260                 265                 270

Asp Lys Asn Val Ser Pro Glu Ala Arg His Pro Leu Val Ala Ala Tyr
        275                 280                 285

Pro Ile Val His Val Asp Met Glu Asn Ile Ile Leu Ser Lys Asn Glu
    290                 295                 300

Asp Gln Ser Thr Gln Asn Thr Asp Ser Gln Thr Arg Thr Ile Ser Lys
305                 310                 315                 320

Asn Thr Ser Thr Ser Arg Thr His Thr Ser Glu Val His Gly Asn Ala
                325                 330                 335

Glu Val His Ala Ser Phe Phe Asp Ile Gly Gly Ser Val Ser Ala Gly
            340                 345                 350

Phe Ser Asn Ser Asn Ser Ser Thr Val Ala Ile Asp His Ser Leu Ser
        355                 360                 365
```

Leu Ala Gly Glu Arg Thr Trp Ala Glu Thr Met Gly Leu Asn Thr Ala
    370                 375                 380

Asp Thr Ala Arg Leu Asn Ala Asn Ile Arg Tyr Val Asn Thr Gly Thr
385                 390                 395                 400

Ala Pro Ile Tyr Asn Val Leu Pro Thr Thr Ser Leu Val Leu Gly Lys
                405                 410                 415

Asn Gln Thr Leu Ala Thr Ile Lys Ala Lys Glu Asn Gln Leu Ser Gln
            420                 425                 430

Ile Leu Ala Pro Asn Asn Tyr Tyr Pro Ser Lys Asn Leu Ala Pro Ile
        435                 440                 445

Ala Leu Asn Ala Gln Asp Asp Phe Ser Ser Thr Pro Ile Thr Met Asn
    450                 455                 460

Tyr Asn Gln Phe Leu Glu Leu Glu Lys Thr Lys Gln Leu Arg Leu Asp
465                 470                 475                 480

Thr Asp Gln Val Tyr Gly Asn Ile Ala Thr Tyr Asn Phe Glu Asn Gly
                485                 490                 495

Arg Val Arg Val Asp Thr Gly Ser Asn Trp Ser Glu Val Leu Pro Gln
            500                 505                 510

Ile Gln Glu Thr Thr Ala Arg Ile Ile Phe Asn Gly Lys Asp Leu Asn
        515                 520                 525

Leu Val Glu Arg Arg Ile Ala Ala Val Asn Pro Ser Asp Pro Leu Glu
    530                 535                 540

Thr Thr Lys Pro Asp Met Thr Leu Lys Glu Ala Leu Lys Ile Ala Phe
545                 550                 555                 560

Gly Phe Asn Glu Pro Asn Gly Asn Leu Gln Tyr Gln Gly Lys Asp Ile
                565                 570                 575

Thr Glu Phe Asp Phe Asn Phe Asp Gln Gln Thr Ser Gln Asn Ile Lys
            580                 585                 590

Asn Gln Leu Ala Glu Leu Asn Ala Thr Asn Ile Tyr Thr Val Leu Asp
        595                 600                 605

Lys Ile Lys Leu Asn Ala Lys Met Asn Ile Leu Ile Arg Asp Lys Arg
    610                 615                 620

Phe His Tyr Asp Arg Asn Asn Ile Ala Val Gly Ala Asp Glu Ser Val
625                 630                 635                 640

Val Lys Glu Ala His Arg Glu Val Ile Asn Ser Ser Thr Glu Gly Leu
                645                 650                 655

Leu Leu Asn Ile Asp Lys Asp Ile Arg Lys Ile Leu Ser Gly Tyr Ile
            660                 665                 670

Val Glu Ile Glu Asp Thr Glu Gly Leu Lys Glu Val Ile Asn Asp Arg
        675                 680                 685

Tyr Asp Met Leu Asn Ile Ser Ser Leu Arg Gln Asp Gly Lys Thr Phe
    690                 695                 700

Ile Asp Phe Lys Lys Tyr Asn Asp Lys Leu Pro Leu Tyr Ile Ser Asn
705                 710                 715                 720

Pro Asn Tyr Lys Val Asn Val Tyr Ala Val Thr Lys Glu Asn Thr Ile
                725                 730                 735

Ile Asn Pro Ser Glu Asn Gly Asp Thr Ser Thr Asn Gly Ile Lys Lys
            740                 745                 750

Ile Leu Ile Phe Ser Lys Lys Gly Tyr Glu Ile Gly
        755                 760

<210> SEQ ID NO 10
<211> LENGTH: 735

```
<212> TYPE: PRT
<213> ORGANISM: Bacillus anthracis
<220> FEATURE:
<221> NAME/KEY: MISC_FEATURE
<223> OTHER INFORMATION: Anthrax Protective Antigen without signal
      peptide andincluding N682A/D683A mutations

<400> SEQUENCE: 10

Glu Val Lys Gln Glu Asn Arg Leu Leu Asn Glu Ser Glu Ser Ser Ser
1               5                   10                  15

Gln Gly Leu Leu Gly Tyr Tyr Phe Ser Asp Leu Asn Phe Gln Ala Pro
            20                  25                  30

Met Val Val Thr Ser Ser Thr Thr Gly Asp Leu Ser Ile Pro Ser Ser
        35                  40                  45

Glu Leu Glu Asn Ile Pro Ser Glu Asn Gln Tyr Phe Gln Ser Ala Ile
    50                  55                  60

Trp Ser Gly Phe Ile Lys Val Lys Lys Ser Asp Glu Tyr Thr Phe Ala
65                  70                  75                  80

Thr Ser Ala Asp Asn His Val Thr Met Trp Val Asp Asp Gln Glu Val
                85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
    210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Gln Thr Arg Thr
        275                 280                 285

Ile Ser Lys Asn Thr Ser Thr Ser Arg Thr His Thr Ser Glu Val His
    290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
            340                 345                 350

Asn Thr Ala Asp Thr Ala Arg Leu Asn Ala Asn Ile Arg Tyr Val Asn
        355                 360                 365

Thr Gly Thr Ala Pro Ile Tyr Asn Val Leu Pro Thr Thr Ser Leu Val
```

-continued

```
    370                 375                 380

Leu Gly Lys Asn Gln Thr Leu Ala Thr Ile Lys Ala Lys Glu Asn Gln
385                 390                 395                 400

Leu Ser Gln Ile Leu Ala Pro Asn Asn Tyr Tyr Pro Ser Lys Asn Leu
                405                 410                 415

Ala Pro Ile Ala Leu Asn Ala Gln Asp Asp Phe Ser Ser Thr Pro Ile
            420                 425                 430

Thr Met Asn Tyr Asn Gln Phe Leu Glu Leu Glu Lys Thr Lys Gln Leu
        435                 440                 445

Arg Leu Asp Thr Asp Gln Val Tyr Gly Asn Ile Ala Thr Tyr Asn Phe
    450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
                485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
        515                 520                 525

Ile Ala Phe Gly Phe Asn Glu Pro Asn Gly Asn Leu Gln Tyr Gln Gly
    530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
                565                 570                 575

Val Leu Asp Lys Ile Lys Leu Asn Ala Lys Met Asn Ile Leu Ile Arg
            580                 585                 590

Asp Lys Arg Phe His Tyr Asp Arg Asn Asn Ile Ala Val Gly Ala Asp
        595                 600                 605

Glu Ser Val Val Lys Glu Ala His Arg Glu Val Ile Asn Ser Ser Thr
    610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
                645                 650                 655

Asn Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
        675                 680                 685

Ile Ser Asn Pro Asn Tyr Lys Val Asn Val Tyr Ala Val Thr Lys Glu
    690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
                725                 730                 735
```

METHOD OF TREATING A BLADDER CANCER USING A CHIMERIC EGF-TARGETED BACTERIAL TOXIN

CROSS-REFERENCE TO RELATED APPLICATION

This application claims priority to U.S. Provisional Application No. 62/333,438, entitled "METHOD OF TREATING A BLADDER CANCER USING A CHIMERIC EGF-TARGETED BACTERIAL TOXIN" filed on May 9, 2016, the entirety of which is herein incorporated by reference.

TECHNICAL FIELD

The present disclosure is generally related to a therapeutic composition targeting bladder cancer cells. The present disclosure is also generally related to methods of treating a bladder cancer by a therapeutic composition specifically targeting bladder cancer cells expressing the epidermal growth factor receptor.

BACKGROUND

Bladder cancer is the 4th most common cancer in men and 11th most common in women (American Cancer Society. Cancer Facts and Figures 2014. Atlanta: Am. Cancer Soc. (2014)). Approximately 70% of newly diagnosed patients suffer disease recurrence after surgical treatment and more than 20% develop invasive bladder cancer (Yeung et al., (2014) *Pharmacoeconomics* 32 1093-1094). The majority of bladder cancer patients return frequently for office visits, cystoscopic procedures and intravesical treatments. The resulting economic burden on the U.S. health care system is estimated at more than $4 billion per year (Yeung et al., (2014) *Pharmacoeconomics* 32 1093-1094). Therefore, the development of efficient therapeutic strategies against this pathology is highly desirable.

SUMMARY

Briefly described, one aspect of the disclosure encompasses embodiments of a method of delivering a therapeutic agent to a bladder cancer cell in an animal or human patient, said method comprising: administering to an animal or human patient in need thereof a therapeutic composition specifically targeting a cancer cell in the bladder of said patient comprising: a first fusion protein capable of specifically binding to an epidermal growth factor receptor (EGFR) on the surface of a cancer cell and comprising an epidermal growth factor (EGF) polypeptide conjugated to a bacterial toxin polypeptide; a second fusion protein comprising an anthrax Lethal Factor N-terminus ($LF_N$) conjugated to a Diptheria Toxin A (DTA) catalytic domain, and a pharmaceutically acceptable carrier.

In some embodiments of this aspect of the disclosure, the bacterial toxin polypeptide can be a mutant anthrax Protective Antigen (PA') polypeptide, wherein said PA' polypeptide is unable to selectively bind to an anthrax receptor.

In some embodiments of this aspect of the disclosure, the therapeutic composition can be administered to the patient by delivery into the lumen of the bladder via a catheter inserted through the urethra.

In some embodiments of this aspect of the disclosure, the method can further comprise administering to the animal or human patient in need thereof, at least two consecutive doses of the therapeutic composition.

Another aspect of the disclosure encompasses embodiments of a method of treating a bladder cancer in an animal or human patient, said method comprising: administering to an animal or human patient in need thereof a therapeutic composition specifically targeting a cancer cell in the bladder of said patient comprising: a first fusion protein capable of specifically binding to an epidermal growth factor receptor (EGFR) on the surface of a cancer cell and comprising an epidermal growth factor (EGF) polypeptide conjugated to a bacterial toxin polypeptide; a second fusion protein comprising an anthrax Lethal Factor N-terminus ($LF_N$) conjugated to a Diptheria Toxin A (DTA) catalytic domain, and a pharmaceutically acceptable carrier.

In some embodiments of this aspect of the disclosure, the bacterial toxin polypeptide is a mutant anthrax Protective Antigen (PA') polypeptide, wherein said PA' polypeptide is unable to selectively bind to an anthrax receptor.

In some embodiments of this aspect of the disclosure, the method comprises administering to the animal or human patient in need thereof, at least two consecutive doses of the pharmaceutically acceptable composition.

Still another aspect of the disclosure encompasses embodiments of a kit comprising a first container having a first fusion protein capable of specifically binding to an epidermal growth factor receptor (EGFR) on the surface of a cancer cell and comprising an epidermal growth factor (EGF) polypeptide conjugated to a bacterial toxin polypeptide, a second container having a second fusion protein comprising an anthrax Lethal Factor N-terminus ($LF_N$) conjugated to a Diptheria Toxin A (DTA) catalytic domain, and optionally a third container having a pharmaceutically acceptable carrier, and instructions for preparing a therapeutic composition comprising effective amounts of the first and second fusion proteins and the pharmaceutically acceptable carrier, wherein said therapeutic composition is formulated for delivering an effective amount of the therapeutic composition to the lumen of the bladder of a patient in need thereof for modulating the proliferation or viability of cancer cells in said patient.

Yet another aspect of the disclosure encompasses embodiments of a therapeutic composition comprising: a first fusion protein capable of specifically binding to an epidermal growth factor receptor (EGFR) on the surface of a cancer cell and comprising an epidermal growth factor (EGF) polypeptide conjugated to a bacterial toxin polypeptide, a second fusion protein comprising an anthrax Lethal Factor N-terminus ($LF_N$) conjugated to a Diptheria Toxin A (DTA) catalytic domain, and a pharmaceutically acceptable carrier, wherein the therapeutic composition is formulated for delivering an effective amount of the therapeutic composition to the lumen of the bladder of a patient in need thereof for modulating the proliferation or viability of cancer cells in said patient.

In some embodiments of this aspect of the disclosure, the bacterial toxin polypeptide is a mutant anthrax Protective Antigen (PA') polypeptide, wherein said PA' polypeptide is unable to selectively bind to an anthrax receptor.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 1A schematically illustrates the bladder and bladder urothelium architecture. In contrast to normal differentiated umbrella cells, bladder tumor cells are known to be deficient for GAG layer synthesis. Therefore, tumor cells are exposed to the lumen of the bladder and overexpress EGFR.

FIG. 1B schematically illustrates the mechanism of action of the EGF-toxin. The specificity of a mutated version of the anthrax Protective Antigen (PA': oval, unable to recognize the anthrax receptor) is redirected to EGFR by fusion to EGF (star). Following EGFR binding, EGF-PA' assembles as an octamer on the plasma membrane. This complex binds the anthrax Lethal Factor N-terminus ($LF_N$) fused to the catalytic domain of diphtheria toxin (DTA, the $LF_N$-DTA fusion is represented by triangles). Following internalization, the lower pH of the endosome induces a conformational change in the EGF-PA' octamer that promotes its insertion into the endosomal membrane and $LF_N$-DTA translocation into the cytosol. $LF_N$-DTA catalyzes the ADP-ribosylation of the eukaryotic elongation factor 2 (eEF2).

FIG. 1C illustrates that bladder cancer cells can be targeted by EGF and the EGF-toxin. Upper panels: Fluorescent (tetra-methyl-rhodamine: TMR)-EGF was bound and internalized by the human T24 and mouse MB49 bladder cancer cell lines and canine bladder tumor cells in the presence of saline and 50% of corresponding urine, as detected by epifluorescence microscopy. Scale bar: 20 microns. Lower panel: A graph showing 20,000 cells of the indicated origin were plated per well on 6-well plates and incubated for 8 min in presence or absence ("controls") of the indicated reagents in saline supplemented with 50% corresponding urine. After 48 h cell viability was measured by MTT assays and represented as percentage of the control of triplicates.

FIG. 1D illustrates EGFR and Her2 expression levels in bladder cancer cells. The presence of EGFR and Her2 was investigated by Western blotting on whole lysates from T24, MB49 (Wildtype and LE (Low Expression) variant that bears undetectable EGFR levels) and canine tumor cells using specific antibodies (EPR39Y anti-EGFR from Abcam, and HPA001383 anti-Her2 from Sigma). Representative results are shown. Indicated results were quantified by band densitometry of 3 independent determinations. Tubulin and actin were used as loading controls.

FIG. 2A illustrates the EGF-toxin targeting and elimination of human bladder cancer cells.

FIG. 2B illustrates the EGF-toxin binding and specificity: drug-response relationship. Left Panel: Experimental setup was performed incubating serum-starved T24 cells with different concentrations of EGF-PA' for 45 min on ice. Other experimental variables were fixed: incubation with $LF_N$-DTA at 37° C. was conducted for 30 min, and MTT assays were performed 48 h after toxin exposure. Right Panel: To test the EGFR specificity of the EGF-toxin, a 100× excess of unmodified EGF was added to compete EGF-PA' binding to the receptor.

FIG. 2C illustrates the kinetics of toxin assembly and internalization. Experimental setup was conducted by binding EGF-PA' at either $LC_{50}$ (top) or $LC_{100}$ (bottom) concentrations on ice, and allowing complex assembly and internalization for different times before stripping off non-internalized protein and adding complete media. MTT assays were conducted 48 h later.

FIG. 2D illustrates the kinetics of toxin action. Upper panel: $10^4$ cells were incubated with an $LC_{100}$ concentration of EGF-PA' on ice, followed by $LF_N$-DTA at 37° C. for 30 min to allow assembly and uptake of the toxin. MTT assays were performed at the indicated times to monitor cell viability as a function of time. Lower panel: Cells were seeded at confluency on glass coverslips within wells of 6-well plates. EGF-toxin treatment was as described in upper panel. At the indicated time points the cells were fixed, stained and imaged. The cell occupancy (fraction of area cover by cells) was determined using ImageJ software. Average occupancy (± standard deviation) of 3 independent experiments is indicated.

FIGS. 3A-3C illustrate that EGF-toxin induces bladder tumor reduction in dogs afflicted with spontaneous bladder cancer.

FIGS. 3A and 3B are digital images showing immunohistochemical detection of EGFR expression in canine invasive transitional cell carcinoma. Note the striking immunoreactivity in FIG. 3B.

FIG. 3C illustrates ultrasound images captured from a dog before (PRE, top 2 images) and after (POST, bottom 2 images) treatment with EGF-toxin. The 2 images on the left were made in the sagittal plane. The 2 images on the right were made in the transverse plane.

The ultrasound protocol used is standardized for machine, operator, patient position, probe position and angle, degree of bladder distension, and image analysis program. When this standardized protocol was followed, the inter-assay variability was less than 10%. The estimated tumor volume (sagittal area×transverse dorsal-ventral dimension) was 5.7 $cm^3$ pre-treatment and 3.9 $cm^3$ post treatment, yielding a 31% reduction in tumor volume. The trigone area was considerably free of tumor, especially visible on the transverse plane. This change was noted after just one 5-day course of treatment.

FIGS. 4A-4E illustrate the effect of the EGF-toxin on bladder cancer patient and MB49 cells and in a mouse orthotopic model.

Figure 4A:
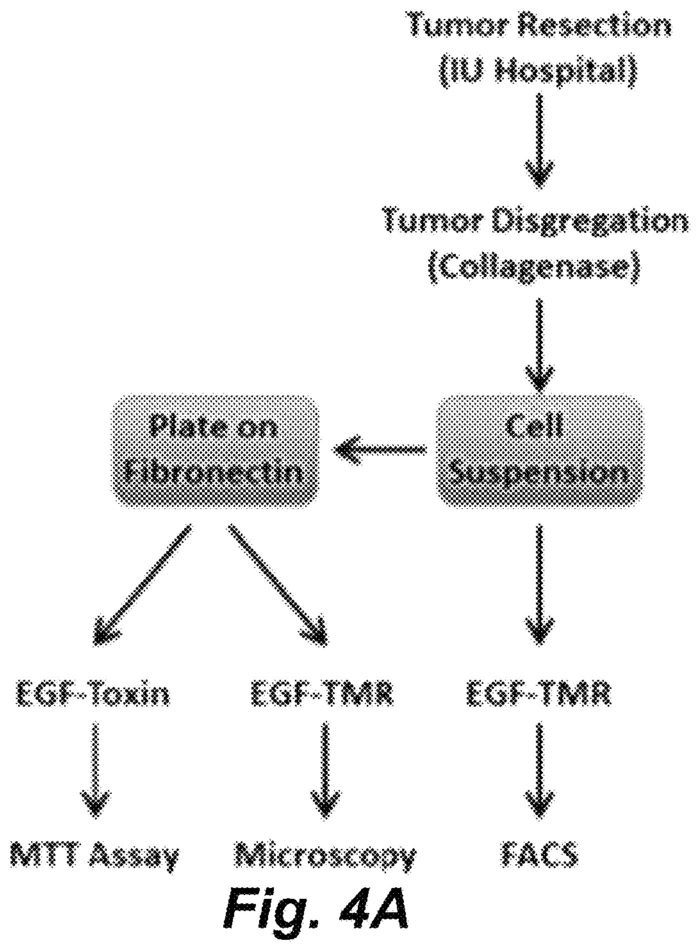

FIG. 4A illustrates a workflow diagram for processing and use of bladder cancer patient samples.

Figure 4B:
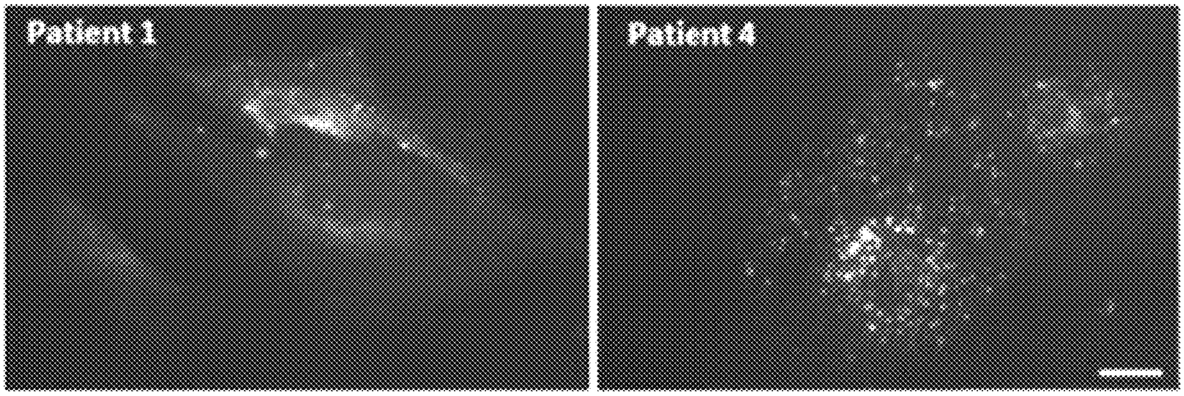
Figure 4C:
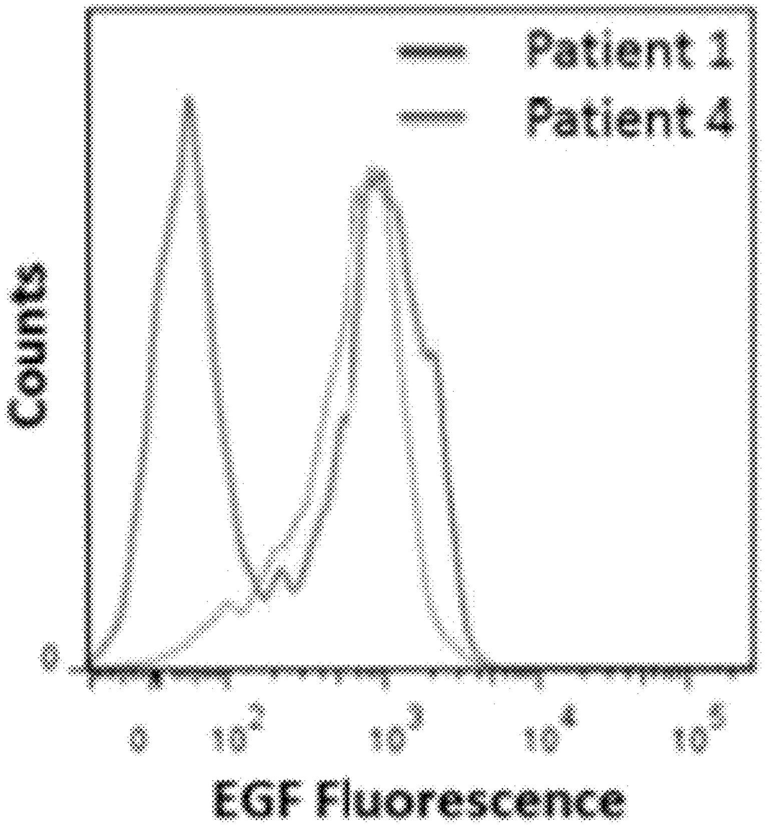

FIGS. 4B-4C illustrate that bladder cancer patient cells bind fluorescent (tetra-methyl-rhodamine: TMR)-EGF as detected by epifluorescence microscopy (FIG. 4B) and flow-cytometry (FIG. 4C). Note the EGF-binding heterogeneities within patient 1 tumor cells: FIG. 4B, left panel shows a cell with substantial EGF-TMR binding (cell above) accompanied by two other with lower binding capacity. A similar result was obtained by FACS analysis, patient 1 exhibited two populations of cells: one with substantial EGF-TMR binding capacity than the other. Patient 4 cells appear more homogeneous with high levels of EGF-TMR binding. Scale bar: 20 microns.

Figure 4D:
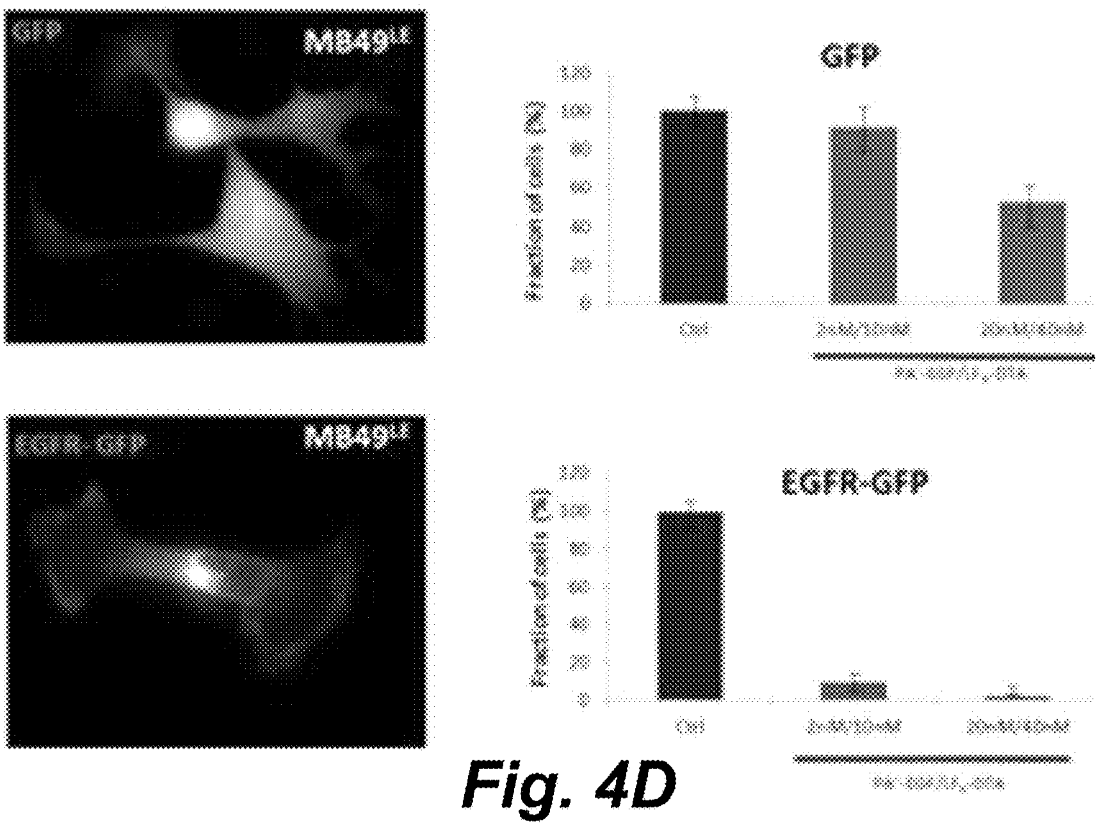

FIG. 4D illustrates that $MB49^{LE}$ cells (very low EGFR expressors) were transfected and led to express GFP or EGFR-GFP (upper and lower panels, respectively). The low sensitivity of the cells to very high doses of EGF-toxin was abrogated by expression of EGFR but not GFP.

Figure 4E:
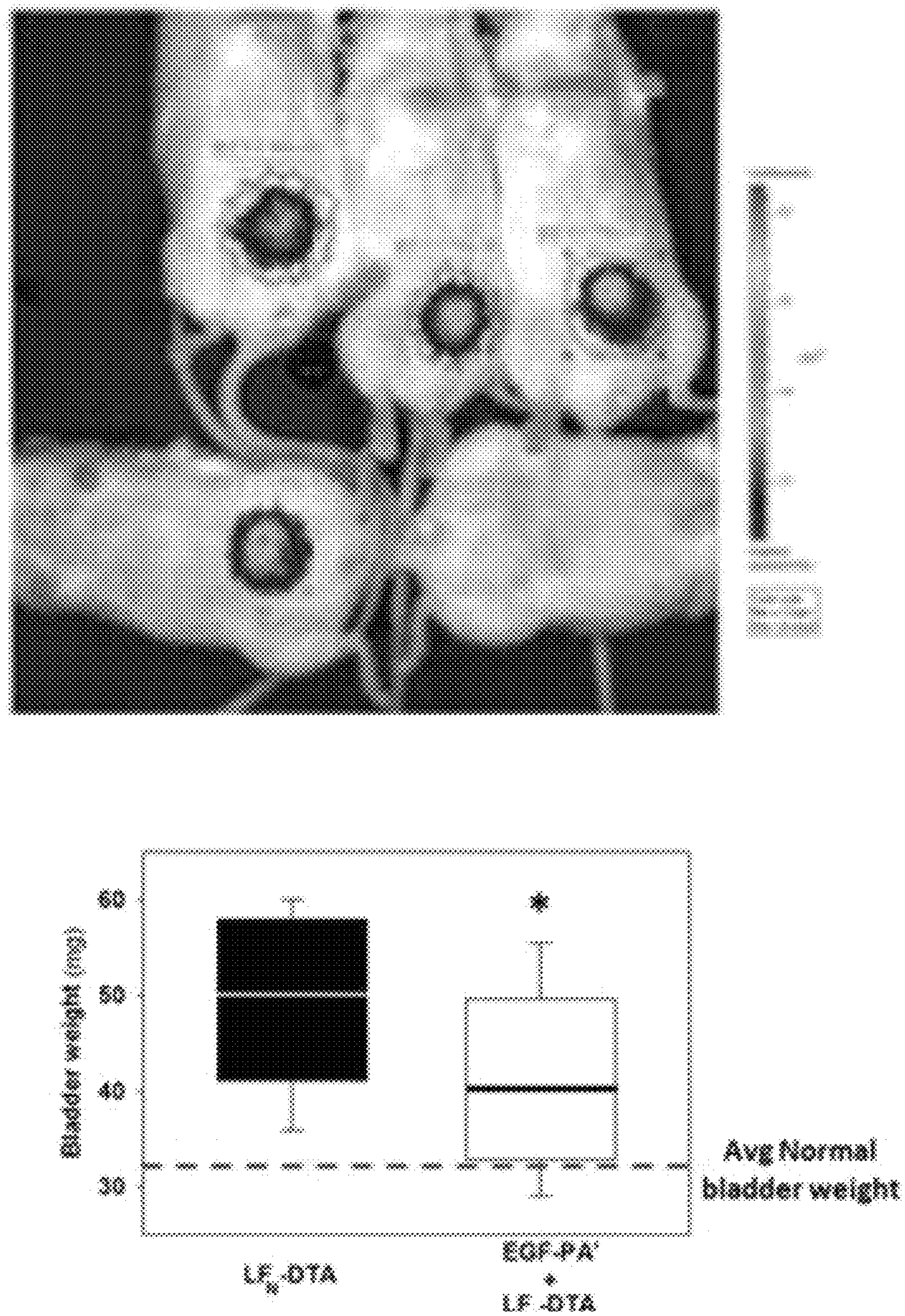

FIG. 4E illustrates a mouse orthotopic model of bladder cancer. Top panel: Implanted bladder tumors were detected in mice bladders by bioluminescence (IVIS imaging) 5 days after instillation of $10^5$ luciferase-expressing, $EGFR^{WT}$-expressing $MB49^{LE}$ cells. Bioluminescence intensity was color-coded according to the scale shown. Control mouse is shown on right bottom corner of the picture. Bottom panel: groups of 10 tumor-bearing mice were treated with 10 nM $LF_N$-DTA in the presence or absence of 2 nM EGF-PA' for 30 min as described in the text. The treatment was repeated 3 times at 24 h intervals. After euthanasia the weights of the tumor-containing bladders were recorded. Average weight of tumor free bladders is indicated. Median weight of treated tumors was significantly lower than the controls (*: $p<0.05$; Wilcoxon test).

FIGS. 5A-5D illustrate a model for the EGF-toxin interaction with EGFR on the surface of bladder cancer cells. Examples of complexes formed upon EGF and EGF-PA' binding to EGFR are shown. Each panel only displays one among multiple possible molecular species present on the cell surface. The abundance of each species will vary depending on several factors described in the main text.

Figure 5A:
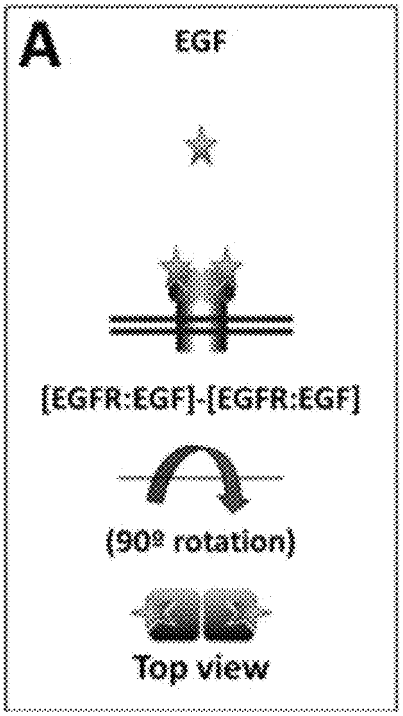

FIGS. 5A-5B schematically illustrate that EGFR dimerizes upon EGF or EGF-PA' binding.

Figure 5C:
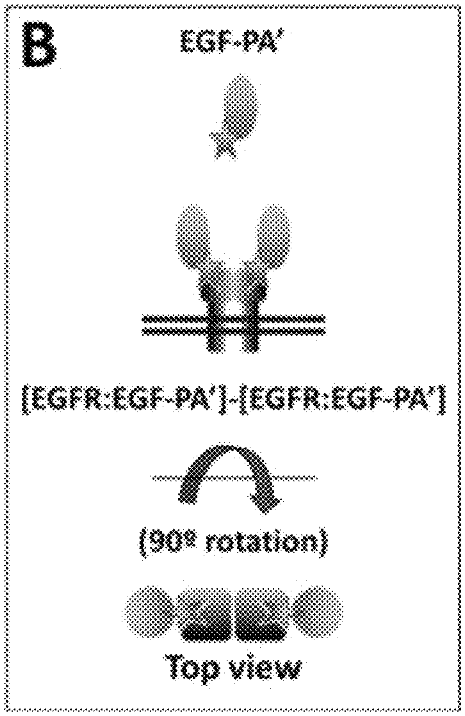
Figure 5C:
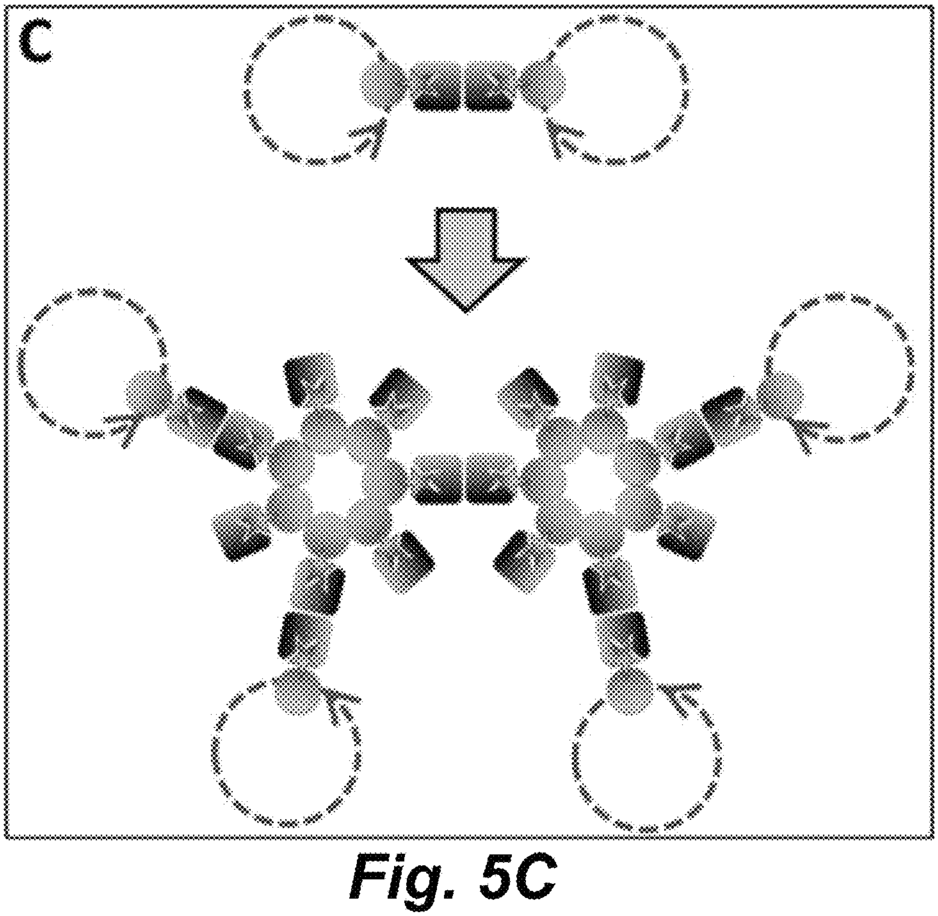

FIG. 5C illustrates multi-pore (MP) complex formation: Upon PA'-heptamer formation (represented by a dotted circle) [EGFR:EGF-PA'] dimers can bridge two or more heptamers. Only one possible MP species is shown (factors such as receptor/ligand concentration and steric hindrance affect the abundance of individual species).

Figure 5D:
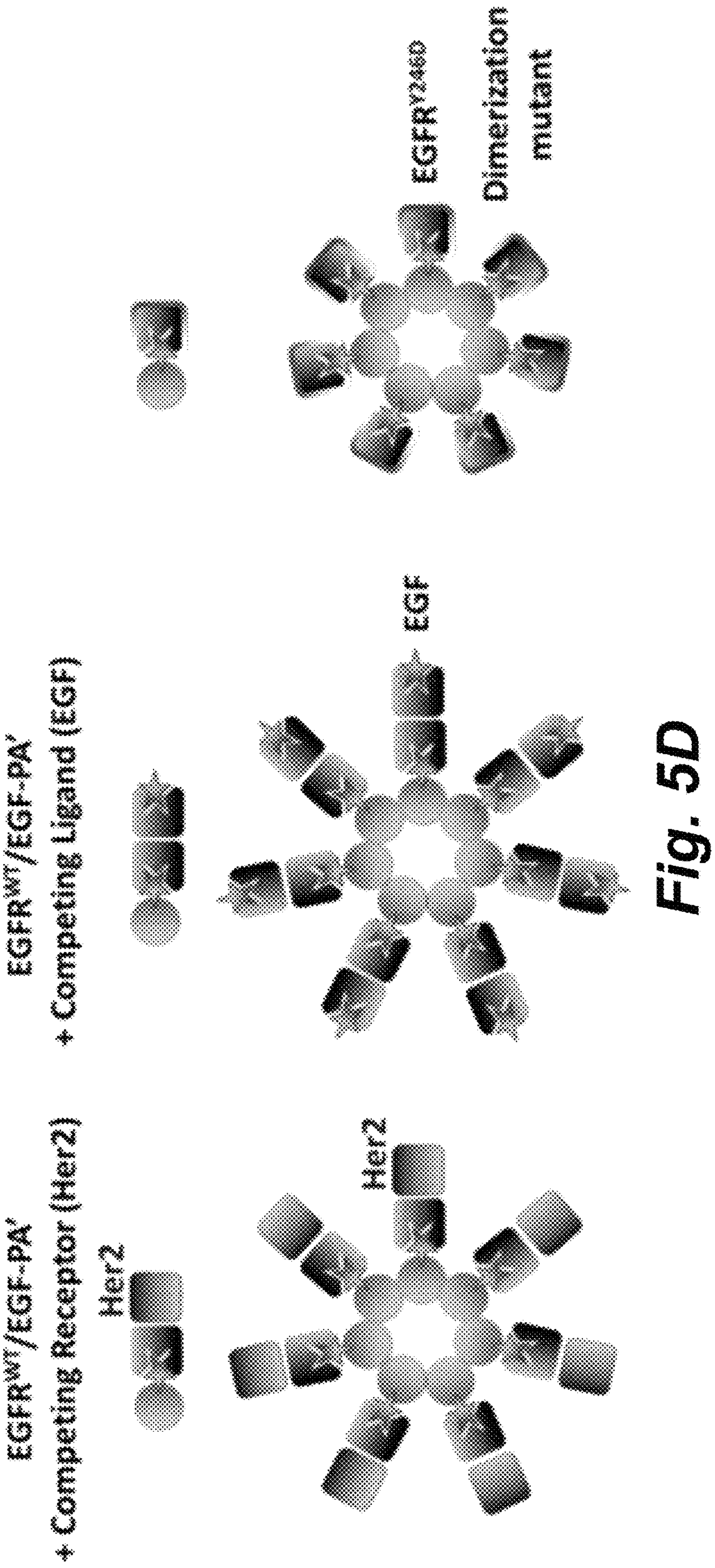

FIG. 5D illustrates examples of complexes that cannot bridge heptamers. These complexes arise from the presence of receptors (e.g. Her2, EGFRY246D) or ligand (e.g. EGF) that can compete off the formation of [EGFR:EGF-PA'] dimers shown in FIG. 5B. Each cartoon depicts one possible resulting complex. The relative proportions of each species (e.g., fully Her2 bound as depicted in the figure versus partially Her2 bound) will depend on relative proportion of each component (e.g., EGFR/Her2). This leads to the absence or different degree of heptamer bridging.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.

Abbreviations

Epidermal growth factor, EGF; Epidermal growth factor receptor, EGFR; EGF-anthrax Protective Antigen mutant fusion-protein, EGF-PA'; mutant Protective Antigen unable to bind anthrax receptor, PA'; anthrax Lethal Factor N-terminus fused to the catalytic domain of Diphtheria Toxin A $LF_N$-DTA; Stochastic Optical Reconstruction Microscopy, STORM;

Definitions

The term "composition" as used herein refers to a product comprising the specified ingredients in the specified amounts, as well as any product which results, directly or indirectly, from combination of the specified ingredients in the specified amounts. Such a term in relation to a pharmaceutical composition is intended to encompass a product comprising the active ingredient(s), and the inert ingredient(s) that make up the carrier, as well as any product which results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the present disclosure and a pharmaceutically acceptable carrier.

A compound or therapeutic composition, such as the EGF-toxin binary composition of the methods of the disclosure may be pure or substantially pure. As used herein, the term "pure" in general means better than 90%, 92%, 93%, 94%, 95%, 96%, 97%, 98% or 99% pure, and "substantially pure" means a compound synthesized such that the compound, as made or as available for consideration into a composition or therapeutic dosage described herein, has only those impurities that cannot readily nor reasonably be removed by conventional purification processes.

The term "formulation" as used herein refers to a composition that may be a stock solution of the components, or a composition, preferably including a dilutant such as water or other pharmaceutically acceptable carrier that may be available for distribution including to a patient or physician.

The terms "subject", "individual", or "patient" as used herein are used interchangeably and refer to an animal, preferably a warm-blooded animal such as a mammal. Mammal includes without limitation any members of the Mammalia. A mammal, as a subject or patient in the present disclosure, can be from the family of Primates, Carnivora, Proboscidea, Perissodactyla, Artiodactyla, Rodentia, and Lagomorpha. Mammalian species that can benefit from the disclosed methods of treatment include, and are not limited to, apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. The term "patient" is intended to include such human and non-human mammalian species, especially those individuals in need of therapeutic treatment using the compositions and methods of the disclosure.

In the context of certain aspects of the disclosure, the term "subject" generally refers to an individual who will receive or who has received treatment (e.g., administration of a compound of the disclosure, and optionally one or more other agents) for a condition characterized by a cancer. In certain aspects, a subject may be a healthy subject. Typical subjects for treatment include persons susceptible to, suffering from or that have suffered a disease disclosed herein. A subject may or may not have a genetic predisposition for a disease disclosed herein.

The term "healthy subject" means a subject, in particular a mammal, having no diagnosed disease, disorder, infirmity, or ailment, more particularly a disease, disorder, infirmity or ailment known to impair or otherwise diminish memory.

The term "diagnosed" as used herein, refers to the recognition of a disease by its signs and symptoms (e.g., resistance to conventional therapies), or genetic analysis, pathological analysis, histological analysis, and the like.

The terms "administering" and "administration" as used herein refer to a process by which a therapeutically effective amount of a compound of the disclosure or compositions contemplated herein are delivered to a subject for prevention and/or treatment purposes. Compositions are administered in accordance with good medical practices taking into account the subject's clinical condition, the site and method of administration, dosage, patient age, sex, body weight, and other factors known to physicians.

The term "delivering to a cell" as used herein refers to the direct targeting of a cell with a small molecule compound, a nucleic acid, a peptide or polypeptide, or a nucleic acid capable of expressing an inhibitory nucleic acid or polypeptide by systemic targeted delivery for in vivo administration, or by incubation of the cell or cells with said effector ex vivo or in vitro. In particular, the compositions of the disclosure comprise the EGF fragments that can specifically bind to the EGF receptor on the surface of certain cells, and therefore target said cells.

The terms "co-administration" or "co-administered" as used herein refer to the administration of at least two compounds or agent(s) or therapies to a subject. In some embodiments, the co-administration of two or more agents/therapies is concurrent. In other embodiments, a first agent/therapy is administered prior to a second agent/therapy in this aspect, each component may be administered separately, but sufficiently close in time to provide the desired effect, in particular a beneficial, additive, or synergistic effect. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s). In the context of the disclosure, co-administration may further refer to the delivery to a bladder of a patient the two fusion proteins (EGF-PA' and the $LF_N$-DTA) in a single volume of a pharmaceutically acceptable carrier.

The methods and compositions of the disclosure may incorporate additional pharmacologically active agents (such as for adjunctive therapy), in addition to an EGF-toxin fusion protein as herein disclosed. For example, the additional pharmacologically active agent can be co-administered consecutively or simultaneously (e.g., in the same formulation or different formulations. As used herein, the term "additional pharmacologically active agent" refers to any agent, such as a drug, capable of having a physiologic effect (e.g., a therapeutic or prophylactic effect) on prokaryotic or eukaryotic cells, in vivo or in vitro, including, but without limitation, chemotherapeutics, toxins, radiotherapeutics, radiosensitizing agents, gene therapy vectors, antisense nucleic acid constructs or small interfering RNA, imaging agents, diagnostic agents, agents known to interact with an intracellular protein, polypeptides, and polynucleotides.

The additional pharmacologically active agent can be selected from a variety of known classes of drugs, including, for example, analgesics, anesthetics, anti-inflammatory agents, anthelmintics, anti-arrhythmic agents, antiasthma agents, antibiotics (including penicillins), anticancer agents (including Taxol), anticoagulants, antidepressants, antidiabetic agents, antiepileptics, antihistamines, antitussives, antihypertensive agents, antimuscarinic agents, antimycobacterial agents, antineoplastic agents, antioxidant agents, antipyretics, immunosuppressants, immunostimulants, antithyroid agents, antiviral agents, anxiolytic sedatives (hypnotics and neuroleptics), astringents, bacteriostatic agents, beta-adrenoceptor blocking agents, blood products and substitutes, bronchodilators, buffering agents, cardiac inotropic agents, chemotherapeutics, contrast media, corticosteroids, cough suppressants (expectorants and mucolytics), diagnostic agents, diagnostic imaging agents, diuretics, dopaminergics (antiparkinsonian agents), free radical scavenging agents, growth factors, haemostatics, immunological agents, lipid regulating agents, muscle relaxants, proteins, peptides and polypeptides, parasympathomimetics, parathyroid calcitonin and biphosphonates, prostaglandins, radio-pharmaceuticals, hormones, sex hormones (including steroids), time release binders, anti-allergic agents, stimulants and anoretics, steroids, sympathomimetics, thyroid agents, vaccines, vasodilators, and xanthines.

The term "treating" as used herein refers to reversing, alleviating, or inhibiting the progress of a disease, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a compound or composition of the present disclosure to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above. The purpose of prevention and intervention is to combat the disease, condition, or disorder and includes the administration of an active compound to prevent or delay the onset of the symptoms or complications, or alleviating the symptoms or complications, or eliminating the disease, condition, or disorder.

The term "modulate" refers to the activity of a composition of the disclosure to affect (e.g., to promote or retard) an aspect of cellular function, including, but not limited to, cell growth, proliferation, apoptosis, and the like.

The term "formulation" as used herein refers to a composition that may be a stock solution of the components, or a composition, preferably including a dilutant such as water or other pharmaceutically acceptable carrier that may be available for distribution including to a patient or physician.

The pharmaceutically "effective amount" for purposes herein is thus determined by such considerations as are known in the art. For therapeutic methods, the amount of EGF-toxin fusion protein must be effective to achieve improvement including but not limited to total prevention and to improved survival rate or more rapid recovery, or improvement or elimination of symptoms associated with a cancer, and in particular a bladder cancer. In accordance with the present disclosure, a suitable single dose size is a dose that is capable of preventing or alleviating (reducing or eliminating) a symptom or the physical dimensions or viability of a tumor in a patient when administered one or more times over a suitable time period. One of skill in the art can readily determine appropriate single dose sizes for administration based on the size of a mammal and the route of administration.

The term "beneficial pharmacokinetic profile" refers to amounts or doses of a compound of the disclosure that provide levels of the compound or a required dose resulting in therapeutic effects in the prevention, treatment, or control of symptoms of a disease disclosed herein. The term "sustained pharmacokinetic profile" as used herein refers to a length of time efficacious levels of a biologically active compound of the disclosure is in its environment of use. A sustained pharmacokinetic profile can be such that a single or twice daily administration adequately prevents, treats, or controls symptoms of a disease disclosed herein. A beneficial pharmacokinetic profile may, but is not limited to, providing therapeutically effective amounts of the compound of the disclosure in the subject for about 12 to about 48 h, 12 h to about 36 h, or 12 h to about 24 h.

The term "therapeutic effect" as used herein refers to an effect of a composition of the disclosure, in particular a formulation or dosage form, or method disclosed herein. A therapeutic effect may be a sustained therapeutic effect that correlates with a continuous concentration of a compound of the disclosure over a dosing period, in particular a sustained dosing period. A therapeutic effect may be a statistically significant effect in terms of statistical analysis of an effect of a compound of the disclosure versus the effects without the compound.

The terms "pharmaceutically acceptable carrier", "excipient" or "vehicle" as used herein refers to a medium which does not interfere with the effectiveness or activity of an active ingredient and which is not toxic to the hosts to which it is administered. A carrier, excipient, or vehicle includes diluents, binders, adhesives, lubricants, disintegrates, bulking agents, wetting or emulsifying agents, pH buffering agents, and miscellaneous materials such as absorbents that may be needed in order to prepare a particular composition. Examples of carriers etc. include, but are not limited to saline, buffered saline, dextrose, water, glycerol, ethanol, and combinations thereof. The use of such media and agents for an active substance is well known in the art.

The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "unit dosage form" as used herein refers to physically discrete units suitable as unitary dosages for human patients and other mammals with each unit containing a predetermined quantity of active material calculated to produce the desired therapeutic effect in association with suitable pharmaceutical carriers or excipients. The compositions according to the present disclosure may be formulated in a unit dosage form. A single daily unit dose also may be divided into 2 or 3 unit doses that are taken at different times throughout the day, or as a controlled release form, so as to reduce adverse side-effects as much as possible.

The term "dosage form" as used herein refers further to a composition or device comprising a compound of the disclosure and optionally pharmaceutically acceptable carrier(s), excipient(s), or vehicles. A dosage form may be an immediate release dosage form or a sustained release, dosage form. An "immediate release dosage form" refers to a dosage form which does not include a component for sustained release i.e., a component for slowing disintegration or dissolution of an active compound. These dosage forms generally rely on the composition of the drug matrix to effect the rapid release of the active ingredient agent. By "sustained release dosage form" is meant a dosage form that releases active compound for many hours. In an aspect, a sustained dosage form includes a component for slowing disintegration or dissolution of the active compound. A dosage form may be a sustained release formulation, engineered with or without an initial delay period. Sustained release dosage forms may continuously release drug for sustained periods of at least about 4 hours or more, about 6 hours or more, about 8 hours or more, about 12 hours or more, about 15 hours or more, or about 20 hours to 24 hours. In aspects of the disclosure the sustained release form results in administration of a minimum number of daily doses.

The term "polypeptide" as used herein refers to proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). In addition, the protein can include non-standard and/or non-naturally occurring amino acids, as well as other amino acids that may be found in phosphorylated proteins in organisms such as, but not limited to, animals, plants, insects, protists, fungi, bacteria, algae, single-cell organisms, and the like. The non-standard amino acids include, but are not limited to, selenocysteine, pyrrolysine, gamma-aminobutyric acid, carnitine, ornithine, citrulline, homocysteine, hydroxyproline, hydroxylysine, sarcosine, and the like. The non-naturally occurring amino acids include, but are not limited to, trans-3-methylproline, 2,4-methanoproline, cis-4-hydroxyproline, trans-4-hydroxyproline, N-methyl-glycine, allothreonine, methylthreonine, hydroxy-ethylcysteine, hydroxyethylhomocysteine, nitro-glutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine.

The term "fusion" protein" as used herein refers to an engineered (recombinant) polypeptide comprising at least two heterologous domains. As used herein, the term "engineered protein" refers to a non-naturally-occurring polypeptide. The term encompasses, for example, a polypeptide that comprises one or more changes, including additions, deletions or substitutions, relative to a naturally occurring polypeptide, wherein such changes were introduced by recombinant DNA techniques. The term also encompasses a polypeptide that comprises an amino acid sequence generated by man, an artificial protein, a fusions protein, and a chimeric polypeptide. Once expressed, recombinant peptides, polypeptides and proteins can be purified according to standard procedures known to one of ordinary skill in the art, including ammonium sulfate precipitation, affinity columns, column chromatography, gel electrophoresis and the like. Substantially pure compositions of about 50 to 99% homogeneity are preferred, and 80 to 95% or greater homogeneity are most preferred for use as therapeutic agents. Engineered proteins may be produced by any means, including, for example, peptide, polypeptide, or protein synthesis.

The term "cancer", as used herein, shall be given its ordinary meaning, as a general term for diseases in which abnormal cells divide without control. In particular, cancer refers to angiogenesis related cancer. Cancer cells can invade nearby tissues and can spread through the bloodstream and lymphatic system to other parts of the body.

There are several main types of cancer, for example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma is cancer that begins in the cells of the immune system.

When normal cells lose their ability to behave as a specified, controlled and coordinated unit, a tumor is formed. Generally, a solid tumor is an abnormal mass of tissue that usually does not contain cysts or liquid areas (some brain tumors do have cysts and central necrotic areas filled with liquid). A single tumor may even have different populations of cells within it, with differing processes that have gone awry. Solid tumors may be benign (not cancerous), or malignant (cancerous). Different types of solid tumors are named for the type of cells that form them. Examples of solid tumors are sarcomas, carcinomas, and lymphomas. Leukemias (cancers of the blood) generally do not form solid tumors.

Representative cancers include, but are not limited to, bladder cancer, breast cancer, colorectal cancer, endometrial cancer, head and neck cancer, leukemia, lung cancer, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, cerebral astrocytoma, glioblastoma, ependymoma, Ewing's sarcoma family of tumors, germ cell tumor, extracranial cancer, Hodgkin's disease leukemia, acute lymphoblastic leukemia, acute myeloid leukemia, liver cancer, medulloblastoma, neuroblastoma, brain tumors generally, non-Hodgkin's lymphoma, osteosarcoma, malignant fibrous histiocytoma of bone, retinoblastoma, rhabdomyosarcoma, soft tissue sarcomas generally, supratentorial primitive neuroectodermal and pineal tumors, visual pathway and hypothalamic glioma, Wilms' tumor, acute lymphocytic leukemia, adult acute myeloid leukemia, adult non-Hodgkin's lymphoma, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer, small-cell lung cancer, among others. In particular, the compositions and methods of the disclosure herein are advantageous for the targeting and treatment of cancers wherein the cancer cells have expressed EGF receptors thereon. Most advantageously, the compositions and methods herein are advantageously directed against bladder cancer cells A tumor can be classified as malignant or benign. In both cases, there is an abnormal aggregation and proliferation of cells. In the case of a malignant tumor, these cells behave more aggressively, acquiring properties of increased invasiveness. Ultimately, the tumor cells may even gain the ability to break away from the microscopic environment in which they originated, spread to another area of the body (with a very different environment, not normally conducive to their growth), and continue their rapid growth and division in this new location. This is called metastasis. Once malignant cells have metastasized, achieving a cure is more difficult.

The term "bladder cancer" as used herein, refers to a cancerous tumor in the bladder. such as transitional cell carcinoma (TCC), squamous cell carcinoma, adenocarcinoma and combinations thereof. The compositions and method of the disclosure are most advantageously directed to, but not necessarily limited to TCC, but also may be applied against any bladder cancer cell bearing an EGF receptor.

The term "TCC" as used herein, refers to transitional cell carcinoma (also known as urothelial cell carcinoma or UCC). It is a type of cancer that typically occurs in the urinary system: the kidney, urinary bladder, and accessory organs. It is the most common type of bladder cancer and cancer of the ureter, urethra, and urachus. TCC often arises from the transitional epithelium, a tissue lining the inner surface of these hollow organs.

The term "specific binding" as used herein refers to the specific recognition of one molecule, of two different molecules, compared to substantially less recognition of other molecules. Generally, the molecules have areas on their surfaces or in cavities giving rise to specific recognition between the two molecules. Exemplary of specific binding are antibody-antigen interactions, enzyme-substrate interactions, polynucleotide interactions, and so forth.

The term "cell or population of cells" as used herein refers to an isolated cell or plurality of cells excised from a tissue or grown in vitro by tissue culture techniques. Most particularly, a population of cells refers to cells in vivo in a tissue of an animal or human.

The term "contacting a cell or population of cells" as used herein refers to delivering a probe according to the present disclosure to an isolated or cultured cell or population of cells, or administering the probe in a suitable pharmaceutically acceptable carrier to the target tissue of an animal or human. Administration may be, but is not limited to, intravenous delivery, intraperitoneal delivery, intramuscularly, subcutaneously, or by any other method known in the art. One advantageous method is to deliver directly into a blood vessel leading into a target organ or tissue such as a prostate, and so reducing dilution of the probe in the general circulatory system.

Description

Figure 1A:
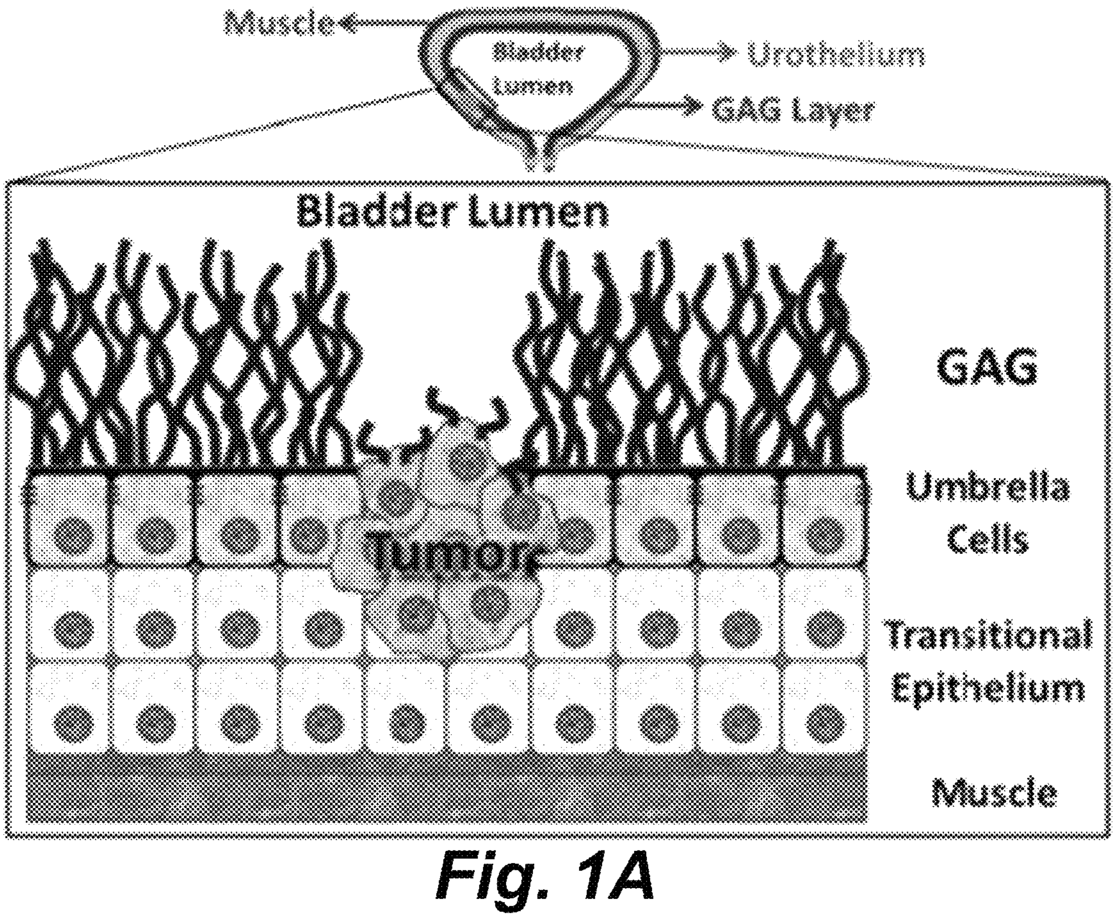
FIGS. 1A-1D illustrate that EGF-toxin targets and eliminates bladder cancer cells.

The bladder displays unique advantages and challenges as a target for therapy. Bladder epithelial cells (FIG. 1A) lining the luminal surface, known as umbrella cells, are engaged in tight junctions that prevent access to the lower transitional cell layers (Romih et al., (2005) *Cell Tissue Res.* 320: 259-268; DeGraff et al., (2013) *Urol. Oncol.* 31: 802-811; Fry C H (2010) in Anthony et al., editors: *The Scientific Basis of Urology*, CRC Press). The urothelium is further isolated from the bladder lumen by a mucin layer comprised of GlycosAmino-Glycans (GAG) that are produced and assembled on the apical surface of the umbrella cells (Romih et al., (2005) *Cell Tissue Res.* 320: 259-268; DeGraff et al., (2013) *Urol. Oncol.* 31: 802-811; Fry C H (2010) in Anthony et al., editors: *The Scientific Basis of Urology*, CRC Press) as illustrated in FIG. 1A. In contrast, malignant bladder cells are usually less differentiated, with less GAG layer synthesis. Therefore, as opposed to normal bladder epithelia, cancer cells are exposed to the lumen of the bladder (FIG. 1A). This leads to increased accessibility of tumor lesions to therapeutic agents, compared to the well-protected normal regions of the bladder. However, constant urine influx and periodic voiding of the bladder limits the beneficial impact of direct instillation of non-targeted therapeutics on tumor cells.

Both superficial and invasive bladder carcinomas overexpress Epidermal Growth Factor (EGF) Receptor (EGFR) (Messing E M (1990) *Cancer Res.* 50: 2530-2537) and, therefore, an EGF-targeted lethal bacterial toxin could be advantageous as an effective agent in bladder cancer therapeutics. However, most EGFR-targeted cytotoxic agents rely on receptor endocytosis to be active; therefore, factors impairing EGFR internalization (e.g., Her2/neu upregulation and EGFR internalization-impairing mutations) can affect their efficacy.

A strategy based on receptor micro-clustering to induce nanoparticle internalization by bladder tumor cells has been developed (Coon et al., (2012) *Int. J. Cancer* 131: 591-600). Importantly, micro-clustering effects can also be elicited by multivalent agents such as the anthrax toxin that (contrary to other toxins such as diphtheria toxin) assembles heptamers/octamers at the plasma membrane thereby inducing its own uptake (Young & Collier (2007) *Annu. Rev. Biochem.* 76: 243-265). Accordingly, an agent that while targeting EGFR, would be able to induce its internalization through an oligomerization (i.e., clustering)-dependent mechanism; and in particular an EGF-anthrax toxin chimera for intravesical instillation was conceived.

In particular, methods of treating a cancer, and especially a bladder cancer, as herein disclosed that use a binary toxin comprising a receptor-ablated pore-forming AB toxin unit fused to a non-toxin-associated receptor-binding ligand specific for a target cell, and a complementary toxin unit capable of associating with the pore-forming toxin unit for delivery of a therapeutic protein to the cytosol of the target cell. Most especially, the methods of the disclosure advantageously use the EGF-toxin binary system EGF-PA'/$LF_N$-DTA, where PA' is a mutant Protective Antigen unable to bind anthrax receptor, and $LF_N$-DTA is anthrax Lethal Factor N-terminus fused to the catalytic domain of Diphtheria Toxin A. The composition and methods of preparing the exemplified EGF-PA' and $LF_N$-DTA fusion proteins of the binary complex are described in U.S. patent application Ser. No. 14/625,386, which was filed on Feb. 18, 2015, the content of which is entirely incorporated herein by reference.

Such a therapeutic protocol is particularly advantageous with respect to safety since the toxin is instilled directly into the lumen of the bladder and not into the bloodstream. Therefore, only the exposed tumor cells are accessed by this agent. In the event of a toxin leak into circulation, the data indicate that due to their heightened sensitivity the dose required for bladder cancer cell elimination is substantially lower than is required for toxin intoxication (e.g., the bladder cancer cell $LC_{100}$ is about 2 nM versus a mice killing dose of about 1 μM (Shoop et al., (2005) *Proc. Natl. Acad. Sci. U.S.A.* 102: 7958-7963). Even if the entire volume of the mouse bladder instillate (80 μl) was to leak into the bloodstream (approximately 1.5 ml), the resulting toxin concentration would be 10,000 times below the lethal dose. In contrast to other toxins, binary toxins (such as anthrax) are safer than one-component agents as dilution greatly decreases the probability of both components reconstituting on normal cells. In addition, when potential toxicity was tested in control animals (mice and dogs) it yielded negative results. Further, administration of the toxin to dogs with spontaneous bladder cancer led to substantial tumor reduction without any discernible toxic side effect.

Figure 1B:
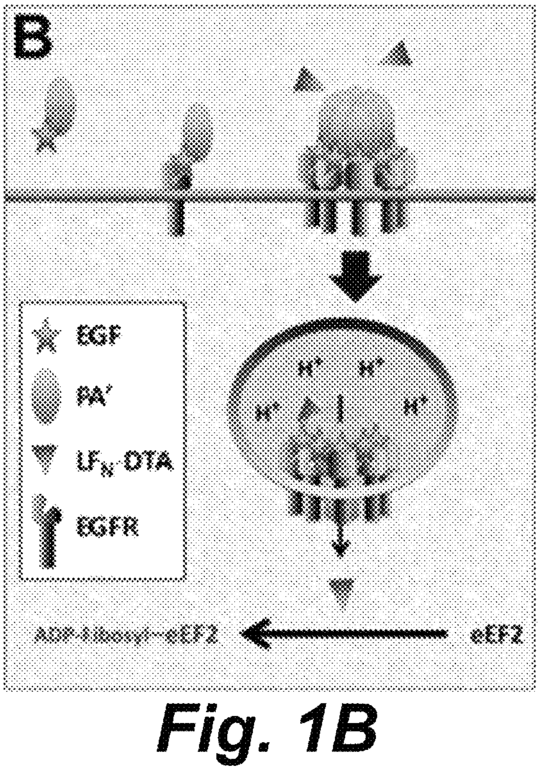

The mechanism of action (Mechaly et al., (2012) *MBio*. 3) of the EGF-toxin system useful in the methods of treatment of the disclosure is depicted in FIG. 1B. Briefly, an EGF-anthrax Protective Antigen mutant fusion-protein (EGF-PA'; where PA' stands for a mutant Protective Antigen unable to bind anthrax receptor) recognizes EGFR, assembles as an heptameric pre-pore complex on the plasma membrane and recruits 2-3 molecules of $LF_N$-DTA (anthrax Lethal Factor N-terminus fused to the catalytic domain of Diphtheria Toxin A; FIG. 1B).

After endocytosis, the lower pH of the endosome induces a conformational change in the EGF-PA' heptamer leading to pore formation and translocation of $LF_N$-DTA molecules, which in turn triggers apoptosis by inactivation of critical elongation factors (FIG. 1B). Significantly, since PA-oligomerization triggers endocytosis, the EGF-toxin bypasses Her2's negative effect on EGFR internalization (Hendriks et al., (2003) *Cancer Res.* 63:1130-1137) and any EGFR mutations that inhibit its endocytosis (factors known to impair the efficacy of other EGF-based strategies).

Figure 1C:
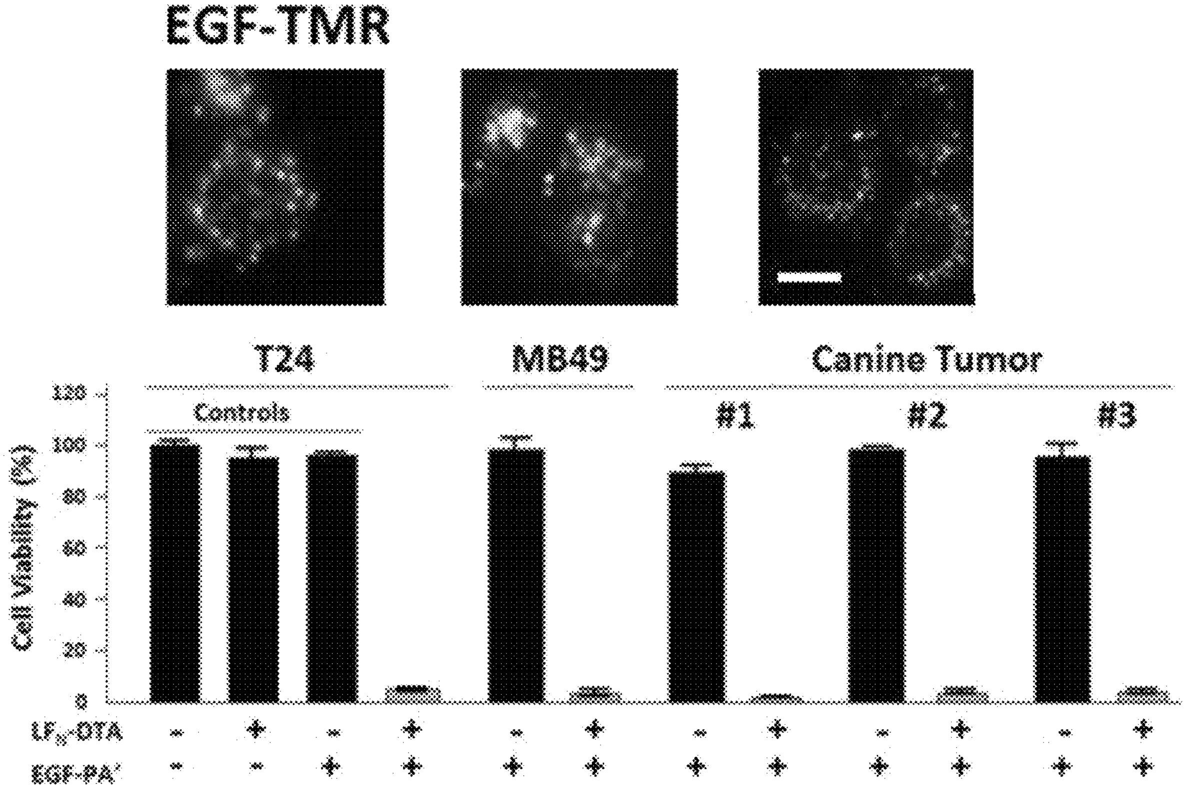

Data indicates that the EGF-toxin can efficiently target and eliminate human, mouse and canine bladder tumor cells (see FIG. 1C), offering a novel, efficacious and fast strategy (a time period of minutes as opposed to hours with current treatments) against both superficial and invasive bladder cancer. Further, the data indicate that even though Her2 was overexpressed in dog tumors, the toxin was effective in vitro and in vivo against canine bladder cancer cells (FIG. 1C). Indeed, three dogs with terminal, treatment-resistant bladder cancer exhibited substantial tumor mass reduction as result of treatment with the EGF-toxin.

The EGF-toxin-based therapeutic strategy of the disclosure is more efficacious than currently available anti-bladder cancer strategies and is more advantageous than other EGF-based approaches (including other toxin formulations) due to its safety and ability to also eliminate Her2-positive cells. In summary, the translational and mechanistic studies proposed in this application provides the basis of an innovative strategy that will be of very high impact in the bladder cancer field. Studies were undertaken to confirm a proof of principle and characterization of the EGF-toxin action on bladder cancer cells, toxicity experiments in animals and investigation of the anti-cancer activity of the toxin by using terminal dogs bearing spontaneous bladder tumors.

Figure 1D:
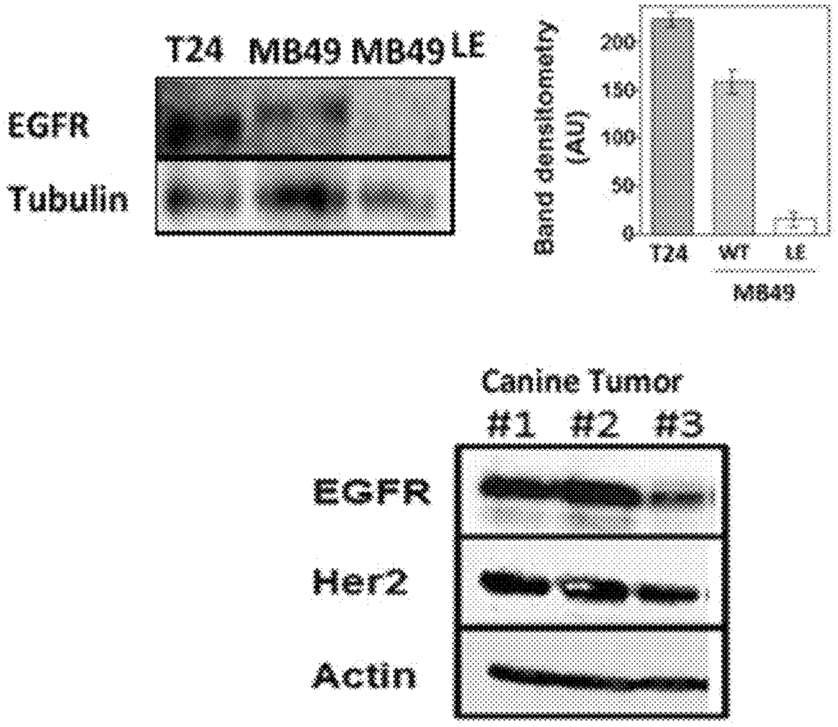

Proof of principle: Soluble EGF and EGF-toxin can target cancer cells in the environment of the bladder. Taking advantage of the fact that human EGF can also bind mouse and dog EGFR, it was determined that fluorescently-labeled hEGF was capable of targeting human, mouse and dog bladder cancer cells under conditions that emulate the environment of the bladder during treatment (i.e., instillation conditions: saline solution+50% of the corresponding urine) as shown in FIG. 1C, upper panels. Accordingly, the EGF-toxin was highly efficient for the elimination of human, mouse and dog cancer cells under the same conditions (FIG. 1C, lower panel). Note that the EGF-toxin was effective against dog tumor cells even when Her2-positive (FIG. 1D, lower panel). This is important as array (Affymatrix canine 2.0) results from 18 dog tumor bladder carcinoma (versus 4 normal) samples have indicate that Her2 is as upregulated as EGFR in these animals.

Figure 2A:
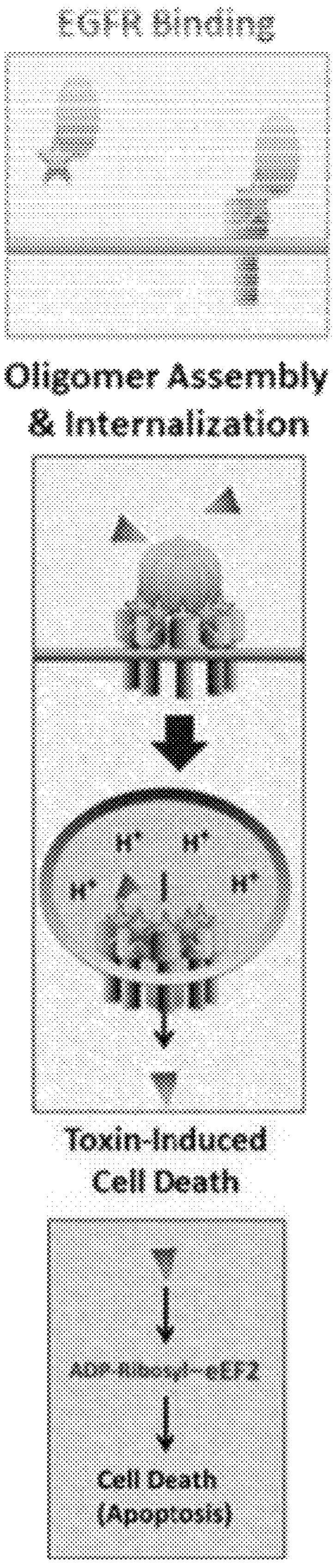
FIGS. 2A-2D illustrates a stepwise approach to the characterization and optimization of the EGF-toxin targeting and elimination of human bladder cancer cells. $2\times10^4$ serum-starved T24 cells (MTT linear range) were plated and incubated with the indicated concentration of EGF-PA' for 45 min on ice to prevent toxin processing and uptake. Following washes to eliminate unbound ligand, the cells are incubated with 10 nM $LF_N$-DTA at 37° C. for the indicated times to allow octamer assembly, internalization and $LF_N$-DTA translocation. Next, non-internalized complexes are stripped off with acidic washes, complete media is added and the cells are kept at 37° C. for the indicated amount of time before MTT assays are conducted.
Figure 2B:
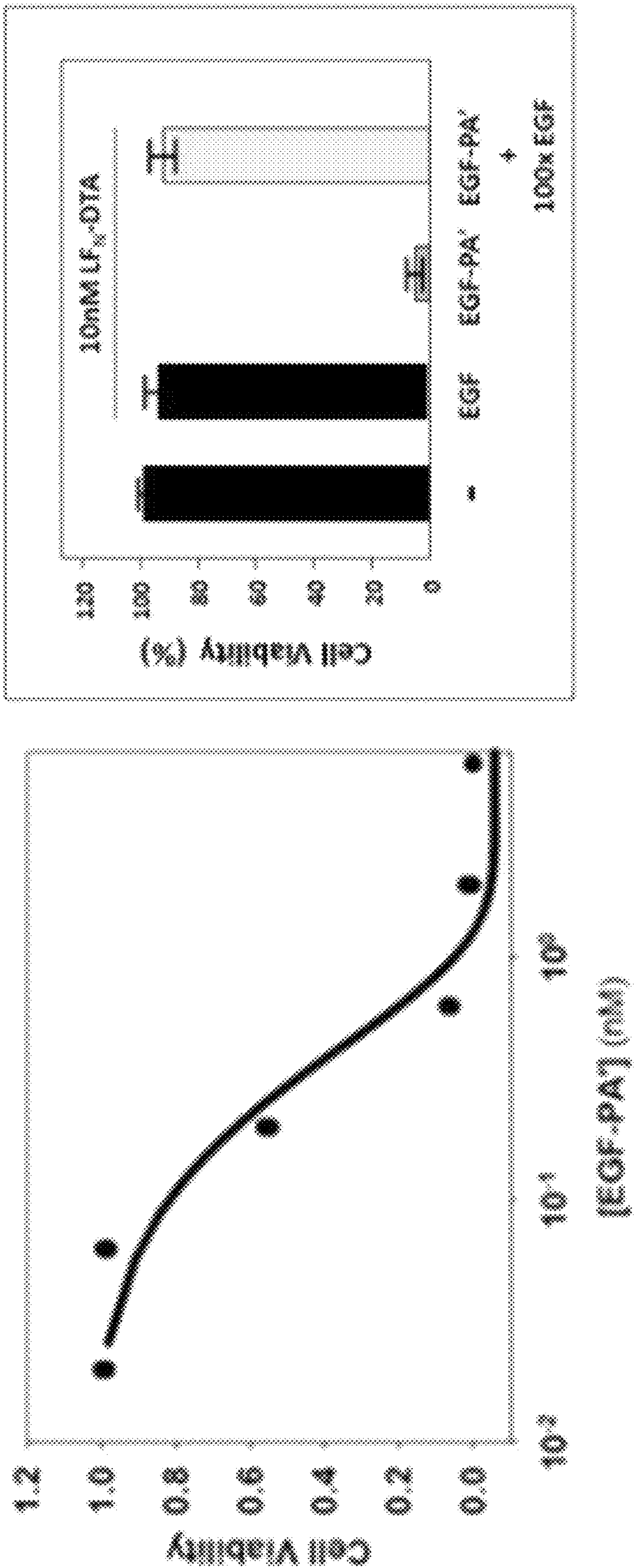

Characterization of the EGF-toxin action on bladder cancer cells: A stepwise approach was taken to characterize three different phases of toxin action on bladder cancer cells (FIG. 2A): binding (FIG. 2B), heptamer assembly/internalization/LFN-DTA translocation (FIG. 2C) and LFN-DTA action (FIG. 2D). Specifically, cells were serum-starved for at least 8 h and incubated with one or multiple EGF-PA' concentrations for 45 min at 4° C. to allow ligand binding, but no further steps of toxin action. Following removal of the unbound ligand, cells were incubated at 37° C. for varying periods to promote pre-pore assembly, complex internalization and $LF_N$-DTA translocation.

TABLE 1

STEPWISE Approach-Analysis of EGF-toxin action on bladder tumor cells

| | Experimental step[a] | Binding Phase Experiments (FIG. 2B) | Assembly/ Internalization and Translocation Phase Experiments (FIG. 2C) | Toxin Action Phase Experiments (FIG. 2D) |
|---|---|---|---|---|
| A | [EGF-PA'] used at 4° C.[b] | Variable (0-20 nM) | $LC_{50}$ or $LC_{100}$ | $LC_{100}$ |
| | Removal of unbound ligand[c] | | | |
| B | Duration of 37° C. incubation with $LF_N$-DTA | 30 min[d] | Variable (0-30 min) | [d] |
| | Removal of non-internalized complexes[c] | | | |
| C | Duration of 37° C. incubation | 48 h[d] | 48 h[d] | Variable (0-48 h) |

[a]See text for general protocol description. Steps A, B and C are adapted according to the toxin action phase studied

[b]Concentration of EGF-PA' incubated for 45 min at 4° C. with bladder cancer cells. Specific $LC_{50}$ and $LC_{100}$ values are provided in Table II.

[c]Same conditions for all experiments.

[d]Time estimate based on published reports by other authors using different cell types and conditions (McCluskey et al., (2013) Mol. Oncol. 7: 440-451).

Ligand not internalized during this incubation period was stripped off using an acidic wash as previously described (Coon et al., (2012) *Int. J. Cancer* 131: 591-600) (the efficiency of this wash was controlled by monitoring the removal of receptor-bound EGF-TMR in a parallel sample). The cells were incubated at 37° C. in complete media for different amounts of time and subjected to MTT cell viability or cell imaging (FIGS. 2A-2D).

This general protocol according to Table 1 was adapted to dissect different phases of toxin action on bladder tumor cells. Using this experimental set up (FIGS. 2A-2D, Table 1) with T24 human bladder cancer cells the EGF-toxin $LC_{50}$ was determined (FIG. 2B, left and Table 2) and confirmed its EGFR specificity (FIG. 2B, right).

The EGF-toxin $LC_{50}$ for canine bladder cancer cells isolated from spontaneous tumors, mouse MB49WT and MB49LE control was also determined (Table 2).

TABLE 2

| Bladder cancer cells | $LC_{50}$ (nM) | $LC_{100}$ (nm) |
|---|---|---|
| Human T24 | 0.31 ± 0.05 | 2.2 ± 0.5 |
| Mouse MB49$^{wt}$ | 0.21 ± 0.02 | 1.9 ± 0.2 |
| MB49$^{Lea}$) | 20 ± 6 | 205 ± 29 |
| Spontaneous canine | 0.33 ± 0.04 | 2.6 ± 0.4 |

TABLE 2-continued

| Bladder cancer cells | $LC_{50}$ (nM) | $LC_{100}$ (nm) |
|---|---|---|
| tumor cells[b] | 0.54 ± 0.07 | 3.6 ± 0.6 |
| | 0.34 ± 0.07[c] | 2.5 ± 0.7[b] |

[a]MB49[LE]: variant expressing very low levels of EGFR

[b]Cells obtained from disaggregation of tumor biopsies. All samples except one (see note c) were immortalized.

[c]Primary culture obtained from one of the dogs treated with the EGF-toxin.

It is known that more than 90% of the EGFR in cells display an affinity ($K_d$) for EGF of approximately 2 nM. As expected, since the data reflects biological activity, the $LC_{50}$ range value for EGFR-expressing bladder cancer cells (approximately 0.2-0.5 nM; Table 2) is substantially smaller than the $K_d$. This result suggests that is not necessary to bind all receptors in the cell to trigger maximal biological activity.

Figure 2C:
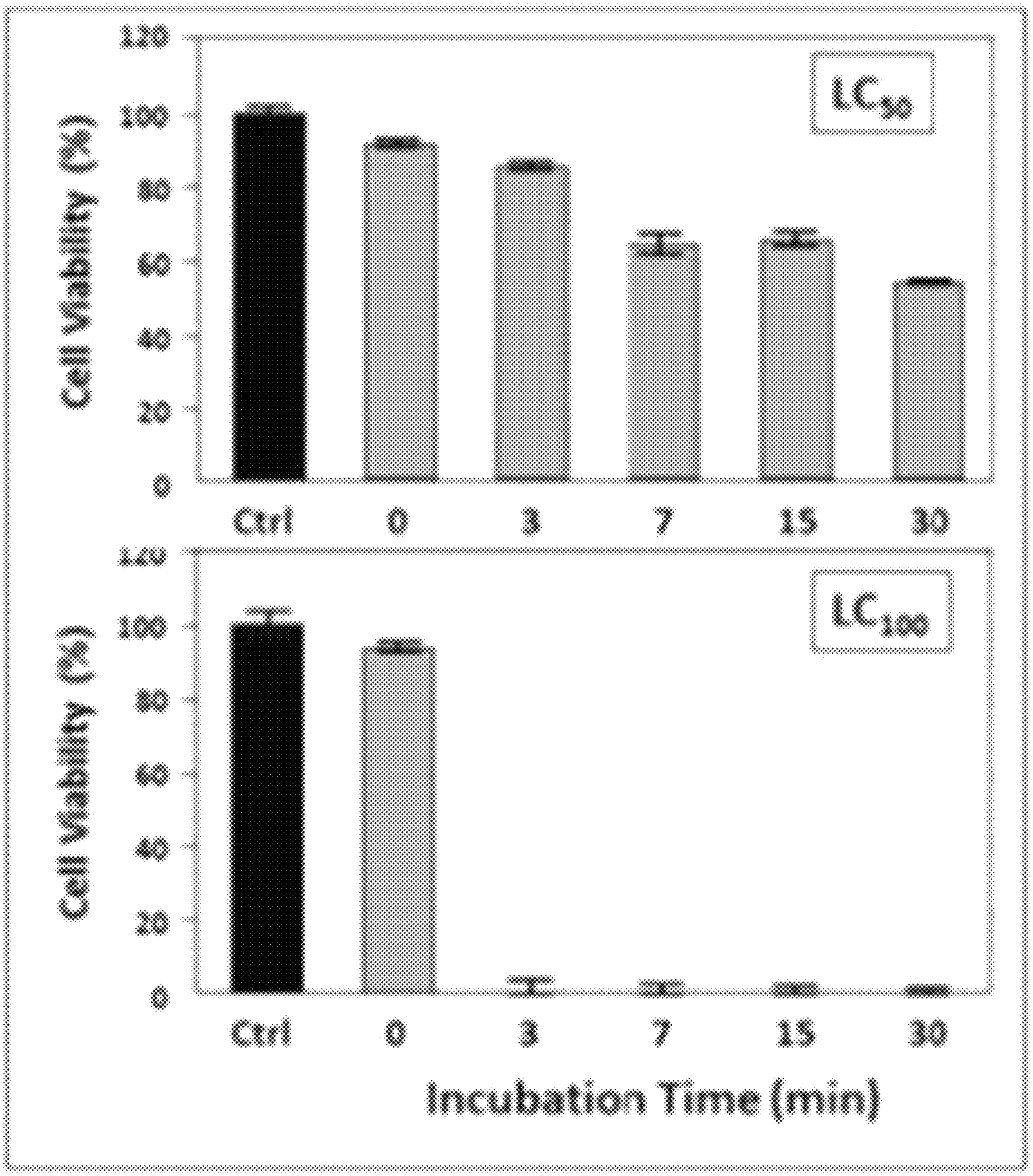
Figure 2D:
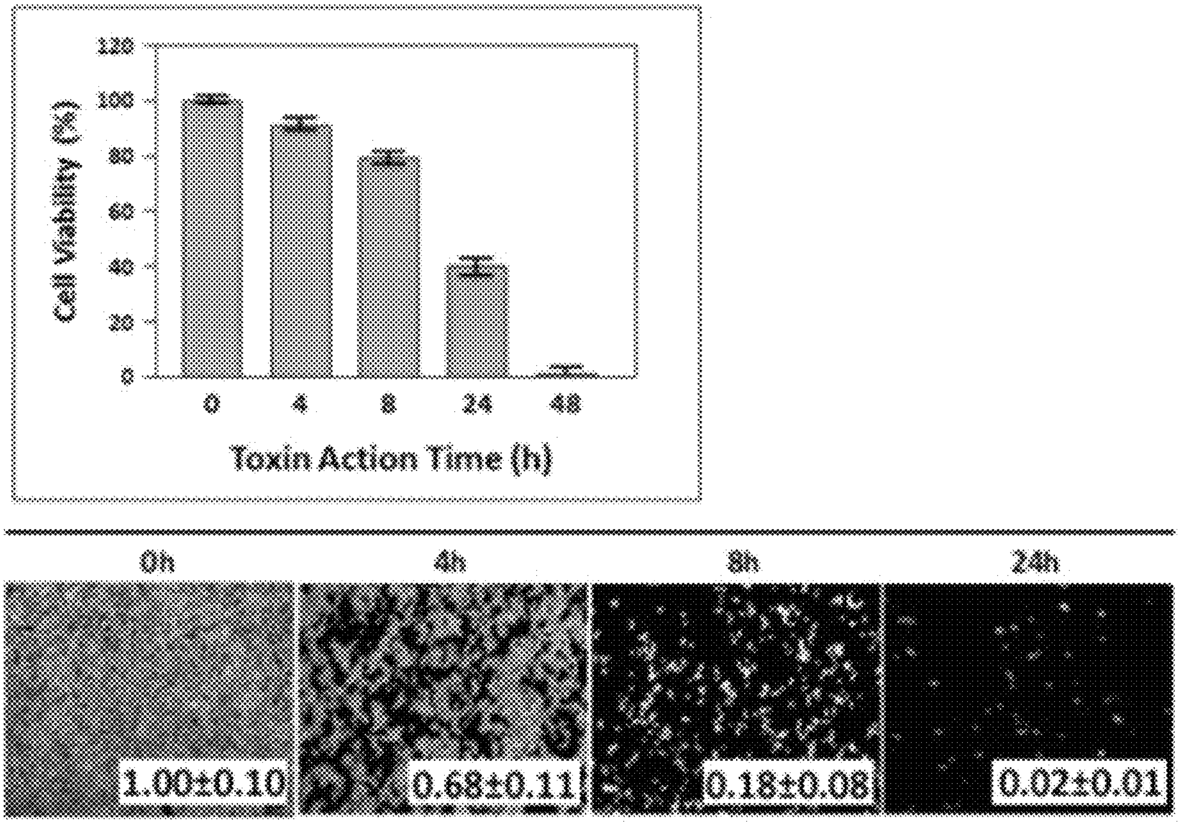

By fixing the EGF-PA' concentration to its $LC_{50}$ value the time-dependence for the assembly/internalization/translocation phase of the EGF-toxin action was determined (FIG. 2C, upper panel). Using EGF-PA' at an absolute lethal concentration ($LC_{100}$), it was established that exposure times to the toxin as short as 3 min assured maximal killing by the toxin (FIG. 2C, lower panel). This result is consistent with the high rate of [EGFR:EGF] complex internalization (Pulse-chase experiments indicate that 5 min after binding, a substantial fraction of EGF can be found in the early endosomal compartment (Burke et al., (2001) *Mol. Biol. Cell.* 12: 1897-1910). Further, the data also indicated that at this dose, the amount of pore assembled and the fraction of $LF_N$-DTA released into the cytosol during this exposure time is sufficient to assure maximal tumor cell elimination. Therefore, this strategy represents an advantageous method of specifically delivering such as a therapeutic agent to bladder cancer cells due to its high efficiency, but also due to the possibility of drastically decreasing patient treatment time from hours (as in current therapies) to minutes.

Four hours after removal of the toxin fluorescent annexin-V binding on treated cells was detected, which is a phenomenon indicative of membrane alterations (exposure of phosphatidylserine in outer leaflet) compatible with apoptosis. However, maximal cell death was observed 48 h after exposure to the toxin as measured by MTT assays (FIG. 2D, upper panel). In addition, T24 monolayers were exposed to the EGF-toxin and cell death was monitored periodically and quantitatively by microscopy (FIG. 2D, lower panel). These experiments were complementary to MTT assays as they followed toxin action by direct observation of cell elimination (creation of “holes” in the monolayer).

These experiments also suggest that as early as 4-8 h after first treatment, the outer layer of a putative tumor can be breached to an extent that a second toxin application at this time will access to underlying layers of the tumor mass. In addition, the looser tumor cell junctions would allow deeper tumor penetration of this molecular agent as compared to nanoparticulated agents or bacteria (for example, BCG).

Based on these results and taking into account practical considerations it was decided to space toxin instillations no greater than 24 h from each other during in vivo treatment. As expected, a “treat-like” approach (i.e., simultaneous exposure of the cells to EGF-PA'/$LF_N$-DTA in saline/urine, at 37° C. and without elimination of unbound or non-internalized proteins) did not result in any change in EGF-toxin sensitivity by the studied cells.

Toxicity experiments in control (bladder tumor-free) animals and preliminary testing of the anti-cancer activity of the EGF-toxin using dogs with spontaneous, terminal bladder cancer: As the first step towards in vivo studies, the EGF-toxin was tested for potential adverse effects in tumor-free animals. Specifically, the toxin was instilled into the bladder of 6 mouse and 4 dog control animals. No toxicity was detected in the animals by any assessment method used (including daily observation and physical exam, urinalyses, complete blood counts, or serum biochemical profiles).

Accordingly, three dogs with very bulky (i.e. blocking the exit of urine in two cases), naturally-occurring invasive transitional cell carcinoma (TCC) resistant to conventional therapies were treated (FIGS. 3A-3C). Dogs were monitored for tumor response with a detailed standardized ultrasound protocol (Chun et al., (1997) *J. Vet. Intern. Med.* 11: 279-283) and for toxicity with physical exams, CBCs, serum biochemical profiles, and urinalyses.

Dog 1 was treated with EGF-toxin (20 nM EGF-PA'/40 nM $LF_N$-DTA, daily for 5 days) and showed a 40% reduction in tumor volume. Dog 2 only received two of the planned five doses due to progression of a comorbid condition, but the tumor mass still decreased in volume by 20%. Dog 3 exhibited three bladder tumors, and after being treated as above, showed 10% and 33% reductions in the volumes of two tumor masses and stabilization of the third mass, as shown in FIG. 3C). Thus, all of the dogs treated with the EGF-toxin showed tumor mass reduction even when multiple tumors were present.

Significantly, while the tumors had been resistant to conventional treatments, in some cases they reached a 10% per day rate of reduction of very bulky tumors; i.e., substantial absolute mass elimination. This response after a single treatment cycle (or less) is especially significant because TCC in dogs closely mimics human invasive bladder cancer in behavior and treatment response. Importantly, the EGF-toxin treatment was well tolerated with no signs of adverse effects in any dog treated. Further, a pilot experiment performed with a mouse orthotopic model also revealed a marked reduction in tumor size when comparing mice treated with EGF-toxin versus a placebo, as shown in FIG. 4E.

Taken together, these results indicate that the treatment strategies of the disclosure are advantageous for the treatment of in bladder cancer due to its high efficiency in vitro and in vivo and its lack of sensitivity to the presence of Her2. An additional benefit of the methods of the disclosure is the potential to drastically decrease patient treatment time from hours, as in current therapies, to minutes.

The pharmaceutical compositions of the subject disclosure can be formulated according to known methods for preparing pharmaceutically useful compositions. Furthermore, as used herein, the phrase “pharmaceutically acceptable carrier” means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the disclosure. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), or suitable mixtures thereof. Formulations containing pharmaceutically acceptable carriers are described in a number of sources which are well known and readily available to those skilled in the art. For example, Remington’s Pharmaceutical Sciences (Martin E W, Remington’s Pharmaceutical Sciences, Easton Pa., Mack Publishing Company, 19th ed., 1995) describes formulations that can be used in connection with the subject disclosure. Formulations suitable for administration of the compositions of the present disclosure include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous solutions and suspensions may be prepared from sterile powder, granules, tablets, etc.

For administration in an aqueous solution, the solution should be suitably buffered if necessary and the liquid diluent first rendered isotonic with sufficient saline or glucose. These particular aqueous solutions are especially suitable for intravenous, intramuscular, subcutaneous, intraperitoneal, and intravesical administration. In this connection, sterile aqueous media which can be employed will be known to those of skill in the art in light of the present disclosure. For example, one dosage could be dissolved in 1 ml of isotonic NaCl solution and either added to 1000 ml of hypodermolysis fluid or catheter delivered to the lumen of a bladder. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

According to the therapeutic methods of the present disclosure, EGF-toxin fusion proteins of the disclosure can be administered and dosed in accordance with good medical practice, taking into account the clinical condition of the individual patient, the site and method of administration, scheduling of administration, patient age, sex, body weight, and other factors known to medical practitioners.

Dosage

Therapeutic efficacy and toxicity of compositions, compositions and methods of the disclosure may be determined by standard pharmaceutical procedures in cell cultures or with experimental animals such as by calculating a statistical parameter such as the $ED_{50}$ (the dose that is therapeutically effective in 50% of the population) or $LD_{50}$ (the dose lethal to 50% of the population) statistics. The therapeutic index is the dose ratio of therapeutic to toxic effects and it can be expressed as the $ED_{50}/LD_{50}$ ratio. Pharmaceutical compositions which exhibit large therapeutic indices are preferred. By way of example, one or more of the therapeutic effects can be demonstrated in a subject or disease model by the screening methods of the disclosure.

The present disclosure provides dosage forms, formulations, and methods that provide advantages and/or beneficial pharmacokinetic profiles, more particularly sustained pharmacokinetic profiles. A composition of the disclosure can be utilized in dosage forms in pure or substantially pure form, in the form of its pharmaceutically acceptable salts, and also in other forms including anhydrous or hydrated forms.

A beneficial pharmacokinetic profile may be obtained by administering a formulation or dosage form suitable for once, twice a day, or three times a day, or more administration comprising one or more composition of the disclosure present in an amount sufficient to provide the required concentration or dose of the composition to an environment of use to treat a disease disclosed herein, in particular a cancer.

Embodiments of the disclosure relate to a dosage form comprising one or more compound of the disclosure that can provide peak concentrations of the EGF-toxin I the urine in the bladder lumen of between about 0.001 to 2 mg/ml, 0001 to 1 mg/ml, 0.0002 to 2 mg/ml, 0.005 to 2 mg/ml, 001 to 2 mg/ml, 0.05 to 2 mg/ml, 0.001 to 0.5 mg/ml, 0.002 to 1 mg/ml, 0.005 to 1 mg/ml, 0.01 to 1 mg/ml, 005 to 1 mg/ml, or 0.1 to 1 mg/ml.

A subject may be treated with a therapeutic composition of the disclosure or a unit dosage thereof on substantially any desired schedule. It may be administered one or more times per day, in particular 1 or 2 times per day, once per week, once a month or continuously. However, a subject may be treated less frequently, such as every other day or once a week, or more frequently. A compound or composition may be administered to a subject for about or at least about 24 hours, 2 days, 3 days, 1 week, 2 weeks to 4 weeks, 2 weeks to 6 weeks, 2 weeks to 8 weeks, 2 weeks to 10 weeks, 2 weeks to 12 weeks, 2 weeks to 14 weeks, 2 weeks to 16 weeks, 2 weeks to 6 months, 2 weeks to 12 months, 2 weeks to 18 months, 2 weeks to 24 months, or for more than 24 months, periodically or continuously.

A beneficial pharmacokinetic profile can be obtained by the administration of a formulation or dosage form suitable for once, twice, or three times a day administration, preferably twice a day administration comprising the EGF-toxin composition of the disclosure present in an amount sufficient to provide the requited dose of the EGF-toxin composition. The required dose of a compound of the disclosure administered once twice, three times or more daily can be about 0.01 to 3000 mg/kg, 0.01 to 2000 mg/kg, 0.5 to 2000 mg/kg, about 0.5 to 1000 mg/kg, 0.1 to 1000 mg/kg, 0.1 to 500 mg/kg, 0.1 to 400 mg/kg, 0.1 to 300 mg/kg, 0.1 to 200 mg/kg, 0.1 to 100 mg/kg, 0.1 to 50 mg/kg, 0.1 to 20 mg/kg, 0.1 to 10 mg/kg, 0.1 to 6 mg/kg, 0.1 to 5 mg/kg, 0.1 to 3 mg/kg, 0.1 to 2 mg/kg, 0.1 to 1 mg/kg, 1 to 1000 mg/kg, 1 to 500 mg/kg, 1 to 400 mg/kg, 1 to 300 mg/kg, 1 to 200 mg/kg, 1 to 100 mg/kg, 1 to 50 mg/kg, 1 to 20 mg/kg, 1 to 10 mg/kg, 1 to 6 mg/kg, 1 to 5 mg/kg, or 1 to 3 mg/kg, or 1 to 2.5 mg/kg, or less than or about 10 mg/kg, 5 mg/kg, 2.5 mg/kg, 1 mg/kg, or 0.5 mg/kg twice daily or less Certain dosage forms and formulations may minimize the variation between peak and trough bladder lumen levels of compounds of the disclosure and in particular provide a sustained therapeutically effective amount of the therapeutic EGF-toxin composition.

The disclosure also contemplates a formulation or dosage form comprising amounts of the EGF-toxin compositions of the disclosure that results in therapeutically effective amounts of the compound over a dosing period, in particular a 24 h dosing period. The therapeutically effective amounts of a compound of the disclosure can be between about 0.1 to 1000 mg/kg, 0.1 to 500 mg/kg, 0.1 to 400 mg/kg, 0.1 to 300 mg/kg, 0.1 to 200 mg/kg, 0.1 to 100 mg/kg, 0.1 to 75 mg/kg, 0.1 to 50 mg/kg, 0.1 to 25 mg/kg, 0.1 to 20 mg/kg, 0.1 to 15 mg/kg, 0.1 to 10 mg/kg, 0.1 to 9 mg/kg, 0.1 to 8 mg/kg, 0.1 to 7 mg/kg, 0.1 to 6 mg/kg, 0.1 to 5 mg/kg, 0.1 to 4 mg/kg, 0.1 to 3 mg/kg, 0.1 to 2 mg/kg, or 0.1 to 1 mg/kg. Most advantageously, the compositions of the disclosure are formulated for delivery in liquid form by means of a catheter to the lumen of the bladder of a recipient animal or human patient.

The dosage form or formulation can be in a sterile aqueous or non-aqueous solvent, such as water, isotonic saline, isotonic glucose solution, buffer solution, or other solvents conveniently used for direct administration to the lumen of a bladder.

A composition of the disclosure may be sterilized by, for example, filtration through a bacteria-retaining filter, addition of sterilizing agents to the composition, irradiation of the composition, or heating the composition. Alternatively, the EGF-toxin compositions of the present disclosure may be provided as sterile solid preparations e.g. lyophilized powder, which are readily dissolved in sterile solvent immediately prior to use.

After pharmaceutical compositions have been prepared, they can be placed in an appropriate container and labeled for treatment of an indicated condition. For administration of a composition of the disclosure, such labeling would include amount, frequency, and method of administration.

Kits

According to the disclosure, a kit is also provided by the disclosure. In an aspect, the kit comprises a EGF-toxin composition of the disclosure or a formulation of the disclosure in kit form. The kit can be a package which houses a container which contains the therapeutic agents of the disclosure or formulations of the disclosure and also houses instructions for administering the EGF-toxin compositions or formulations to a subject, particularly to the bladder of an animal or human patient. The disclosure further relates to a commercial package comprising EGF-toxin compositions of the disclosure or formulations of the disclosure together with instructions for simultaneous, separate or sequential use. In particular a label may include amount, frequency, and method of administration.

The disclosure also provides a pharmaceutical pack or kit comprising one or more containers filled with one or more of the ingredients of an EGF-toxin composition of the disclosure to provide a therapeutic effect. Associated with such container(s) can be various written materials such as instructions for use, or a notice in the form prescribed by a governmental agency regulating the labeling, manufacture, use or sale of pharmaceuticals or biological products, which notice reflects approval by the agency of manufacture, use, or sale for human administration.

The disclosure also relates to articles of manufacture and kits containing materials useful for treating a disease disclosed herein. An article of manufacture may comprise a container with a label. Examples of suitable containers include bottles, vials, and test tubes which may be formed from a variety of materials including glass and plastic. A container holds EGF-toxin compositions of the disclosure or formulations of the disclosure which are effective for treating a disease disclosed herein. The label on the container indicates that the EGF-toxin compositions of the disclosure or formulations of the disclosure are used for treating a disease disclosed herein and may also indicate directions for use. In aspects of the disclosure, a medicament or formulation in a container may comprise any of the medicaments or formulations disclosed herein.

One aspect of the disclosure, therefore, encompasses embodiments of a method of delivering a therapeutic agent to a bladder cancer cell in an animal or human patient, said method comprising: administering to an animal or human patient in need thereof a therapeutic composition specifically targeting a cancer cell in the bladder of said patient comprising: a first fusion protein capable of specifically binding to an epidermal growth factor receptor (EGFR) on the surface of a cancer cell and comprising an epidermal growth factor (EGF) polypeptide conjugated to a bacterial toxin polypeptide; a second fusion protein comprising an anthrax Lethal Factor N-terminus ($LF_N$) conjugated to a Diptheria Toxin A (DTA) catalytic domain, and a pharmaceutically acceptable carrier.

In some embodiments of this aspect of the disclosure, the bacterial toxin polypeptide can be a mutant anthrax Protective Antigen (PA') polypeptide, wherein said PA' polypeptide is unable to selectively bind to an anthrax receptor.

In some embodiments of this aspect of the disclosure, the therapeutic composition can be administered to the patient by delivery into the lumen of the bladder via a catheter inserted through the urethra.

In some embodiments of this aspect of the disclosure, the method can further comprise administering to the animal or human patient in need thereof, at least two consecutive doses of the therapeutic composition.

Another aspect of the disclosure encompasses embodiments of a method of treating a bladder cancer in an animal or human patient, said method comprising: administering to an animal or human patient in need thereof a therapeutic composition specifically targeting a cancer cell in the bladder of said patient comprising: a first fusion protein capable of specifically binding to an epidermal growth factor receptor (EGFR) on the surface of a cancer cell and comprising an epidermal growth factor (EGF) polypeptide conjugated to a bacterial toxin polypeptide; a second fusion protein comprising an anthrax Lethal Factor N-terminus ($LF_N$) conjugated to a Diptheria Toxin A (DTA) catalytic domain, and a pharmaceutically acceptable carrier.

In some embodiments of this aspect of the disclosure, the bacterial toxin polypeptide is a mutant anthrax Protective Antigen (PA') polypeptide, wherein said PA' polypeptide is unable to selectively bind to an anthrax receptor.

In some embodiments of this aspect of the disclosure, the method comprises administering to the animal or human patient in need thereof, at least two consecutive doses of the pharmaceutically acceptable composition.

Still another aspect of the disclosure encompasses embodiments of a kit comprising a first container having a first fusion protein capable of specifically binding to an epidermal growth factor receptor (EGFR) on the surface of a cancer cell and comprising an epidermal growth factor (EGF) polypeptide conjugated to a bacterial toxin polypeptide, a second container having a second fusion protein comprising an anthrax Lethal Factor N-terminus ($LF_N$) conjugated to a Diptheria Toxin A (DTA) catalytic domain, and optionally a third container having a pharmaceutically acceptable carrier, and instructions for preparing a therapeutic composition comprising effective amounts of the first and second fusion proteins and the pharmaceutically acceptable carrier, wherein said therapeutic composition is formulated for delivering an effective amount of the therapeutic composition to the lumen of the bladder of a patient in need thereof for modulating the proliferation or viability of cancer cells in said patient.

Yet another aspect of the disclosure encompasses embodiments of a therapeutic composition comprising: a first fusion protein capable of specifically binding to an epidermal growth factor receptor (EGFR) on the surface of a cancer cell and comprising an epidermal growth factor (EGF) polypeptide conjugated to a bacterial toxin polypeptide, a second fusion protein comprising an anthrax Lethal Factor N-terminus ($LF_N$) conjugated to a Diptheria Toxin A (DTA) catalytic domain, and a pharmaceutically acceptable carrier, wherein the therapeutic composition is formulated for delivering an effective amount of the therapeutic composition to the lumen of the bladder of a patient in need thereof for modulating the proliferation or viability of cancer cells in said patient.

In some embodiments of this aspect of the disclosure, the bacterial toxin polypeptide is a mutant anthrax Protective Antigen (PA') polypeptide, wherein said PA' polypeptide is unable to selectively bind to an anthrax receptor.

It should be emphasized that the embodiments of the present disclosure, particularly any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following claims.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

Differences in the EGFR concentration in normal versus tumor cells will be examined to determine the anti-cancer efficacy and selectivity of the EGF-toxin. To determine the in vitro ability of EGF-toxin to eliminate patient bladder cancer, dog and MB49 mouse cells expressing different levels of EGFR will be used. It is predicted that the higher the levels of EGFR, the higher the EGF-toxin sensitivity of the bladder cancer cells will be. Since PA-clustering triggers the [EGFR:EGF-PA'] complex internalization, the treatment strategy of the disclosure is predicted to also work in Her2-positive cells and even with cells expressing EGFR endocytosis mutants. Therefore, levels of EGFR/EGF binding and toxin sensitivity ($LC_{50}$) will be measured in bladder cancer patient cells, dog spontaneous bladder tumor cells and MB49 mouse cells.

Example 2

The effect of naturally-occurring EGFR level heterogeneities within and between patient tumors on the EGF-toxin efficacy can be determined for assessing the translational potential of this novel strategy. To this end, cells from bladder tumors freshly resected from patients can be used, while normal human bladder epithelial primary cells (Lifeline Cell Tech., FC-0079) can be used as control.

Tissue can be minced into approximately 1 mm×1 mm pieces and digested with collagenase+DNAse for 1.5 h with shaking at 37° C. and purified/enriched in viable cells by low-speed centrifugation using standard approaches to produce a tumor cell suspension.

Part of the cells in suspension can be seeded on fibronectin-coated surfaces (FIG. 4A) (fibronectin is a typical component of the extracellular matrix in bladder tumors). These adherent cells can be used to test EGF-toxin killing efficacy (stepwise approach) as in FIG. 2 (i.e., to determine toxin $LC_{50}$ and rate of action in the presence or absence of excess unmodified EGF). They can be also used to measure fluorescent EGF-TMR binding as in FIG. 1C.

Although cells can come from tumor tissue, expression of tumor markers (e.g., GATA3) can be routinely monitored. The data support the existence of EGF-binding heterogeneity within (FIG. 4B; patient 1) and in-between tumors (FIG. 4B; patient 1 versus 4).

The remaining suspension of cells can be used for FACS analysis following binding of EGF-TMR (FIG. 4A-4C). Flow cytometry data also indicate EGF-binding heterogeneities and internalization differences within/in-between tumors (FIG. 4C). EGFR and Her2 in whole cell lysates can also be detected by Western blotting with specific antibodies (as in FIG. 1D). The results can be quantified by band densitometry. Partial EGFR sequencing can also be performed using patient samples focused on identifying EGF binding or internalization mutants.

Taken together, these determinations can be correlated for the development of accompanying diagnosis, prediction of EGF-toxin treatment outcome and to tailor treatment to the patient. Similar procedures can be applied to samples of spontaneous canine tumors. Results obtained with canine samples are shown in FIG. 1C and Table 2 (EGF binding, EGF-toxin LC50, EGFR/Her2 protein levels). These results also use data collected from biopsies from dogs treated with the EGF-toxin (FIG. 1C, Table 2).

Example 3

To determine in vitro the ability of EGF-toxin to eliminate mouse bladder cancer cells expressing different levels and variants of EGFR: The mouse bladder cancer cell line MB49 is suitable for in vitro manipulation of EGFR levels, allowing to directly test toxin-sensitivity as a function of the levels and nature of EGFR variants. Data (FIG. 1C and Table 2) showed that MB49 cells can be targeted and eliminated in a dose-dependent manner by the EGF-toxin compositions of the disclosure. The MB49 cell line can be used rather than T24 since these cells were used for the establishment of an orthotopic bladder cancer model (FIG. 4E). An MB49 cell line variant expressing extremely low levels of EGFR (MB49LE, LE: Low EGFR) has very low sensitivity to the EGF-toxin (FIG. 4D, Table 2). However, the EGF-toxin resistance of MB49LE can be abrogated by transfection with EGFR-GFP (FIG. 4D). Therefore, MB49LE cells can be stably transfected with plasmids encoding for GFP-EGFRWT, GFP-EGFRK721M (internalization deficient mutant), GFP-EGFRY246D (dimerization mutant) and/or RFP-Her2 (cDNA subcloned in the pEpuro plasmid conferring puromycin-resistance for double selection) to generate clones with at least two different levels of expression ["Moderate-Low" (M-L) and "High" (H) as determined by quantitative Western blotting and flow cytometry (see FIG. 1D) for each protein. In addition, binding of fluorescently-labeled EGF can be also monitored as part of each clone characterization. This small collection of stably transfected clones can constitute a resource that can be used throughout the project, and can be made available to the scientific community upon request.

$MB49^{LE}$ clones can be subjected to the stepwise approach as in Example 2 and the example as in FIG. 4D. Specifically, EGF-toxin composition $LC_{50}$ and rate of action (+/− excess of unmodified EGF to verify EGFR-specificity) can be determined as shown in FIGS. 2A-2D. In addition, optimal $LF_N$-DTA concentrations can also be titrated while maintaining EGF-PA' constant at its $LC_{50}$.

Cells with low levels of EGFR (naturally occurring in patients, MB49LE and normal FC-0079 cells, controls for mouse and human cells, respectively) can be less sensitive (higher $LC_{50}$) to the EGF-toxin effects than EGFR expressors (including the internalization/dimerization mutants, as internalization is solely dependent on PA oligomerization), with H being more sensitive to the toxin than ML clones and even more than untransfected MB49LE.

Example 4

To determine the in vivo ability of EGF-toxin to reduce tumor growth in dog bearing spontaneous bladder tumors and a bladder cancer mouse orthotopic model based on MB49 cells expressing different levels of EGFR: The use of two different animal models can be used as no single one can fully replicate the characteristics of both human superficial and invasive bladder cancer. In addition to being suited for studies concerning superficial bladder tumors, mouse orthotopic models are ideal for controlling tumor characteristics based on manipulation of the murine MB49 cell line (used for tumor induction). However, dogs usually present with bladder cancer that closely resembles invasive human bladder cancer.

Mouse model of bladder cancer: Orthotopic bladder tumors are generated in C57BL/6 mice produced as previously described (Sinn et al., (2008) *Cancer Immunol. Immunother.* 57: 573-579) and incorporated herein by reference in its entirety. Briefly, mice covered under PACUC #1112000342 are anesthetized with 100 μl of a 17.5 mg/ml ketamine, 2.5 mg/ml xylazine solution and then catheterized by inserting a 24-gauge i.v. catheter through the urethra and into the bladder lumen. The bladder is then prepared for site-specific tumor adherence with electrocautery.

Under anesthesia, an electrode of 4-0 surgical stainless steel wire is inserted through the catheter far enough to contact the bladder wall. The electrode is attached to a Bovie electrocautery unit which is activated for 4 sec at the lowest coagulation setting. The electrode is removed and bladders are instilled with $10^5$ MB49 cells stably expressing luciferase (Zaharoff et al., (2009) *Cancer Res.* 69: 6192-6199) in 80 μl of RPMI medium.

Intravesical tumor growth are monitored daily by luciferase imaging following intraperitoneal injection of luciferin salt (15 mg/kg (Zaharoff et al., (2009) *Cancer Res.* 69: 6192-6199)) using an IVIS Lumina II imaging equipment (FIG. 4C); and by ultrasound with a VisualSonics 2100 ultrasound system specifically designed to monitor tumor volume in anesthetized mice (Wang et al., (2006) *Urology* 68: 674-681). A chemical depilatory cream (nair) can be used to remove abdominal and thoracic hair, followed by application of Aquasonic ultrasound gel to minimize reflections between the transducer and the skin. Tumor-bearing mice can be randomly assigned to five groups according to Table 3.

TABLE 3

| Group[a] | Treatment[b] | Time of Treatment | Purpose of the Group | Additional Treatment |
|---|---|---|---|---|
| Control 1 | Saline | about | Controls | EGF-TMR[f] |
| Control 2 | EGF-PA' | 3-4 days[d] | | None |
| Control 3 | $LF_N$-DTA | | | |
| Treatment 1 | EGF-PA' + $LF_N$-DTA | | Tumor growth prevention | |
| Treatment 2 | EGF-PA' + $LF_N$-DTA | about 1 week[e] | Tumor growth reduction | |

[a]10 mice/group; [b]EGF-PA' and $LF_n$-DTA (in saline) applied at 2 nM and 10 nM final concentration, respectively; [c]Time post-tumor implantation; [d]Estimated time of early tumor; [e]Estimated time of development of 200 $mm^3$ tumor as detected by ultrasound; [f]Following euthanasia tumors from "Control 1" group is isolated and incubated with 2 nM EGF-PA' for 30 min, washed thrice and processed for immunohistochemistry Bladders can be catheterized and subjected to 80 μl instillations of the indicated solutions ("Treatment" column, Table 3), allowed to dwell for 30 min and washed three times with fresh saline. Treatment can be repeated every day for one week. All surviving mice are euthanized after 2 weeks and the bladders can be weighed and examined grossly for the presence of tumors and subsequently by histology. Experiments are repeated at least 3 times.

Bladder tumors are isolated from mice in control group 1 and incubated with 2 nM EGF-PA' (without $LF_N$-DTA to avoid cell death) for 30 min in saline, washed, processed for immunohistochemistry (it should be noted that the toxin contains an HA epitope tag in the linker region separating EGF from PA') and imaged. This procedure can provide data on tumor penetration by the toxin.

50 mice (3 controls and 2 treatments, Table 3) can be used per experiment and each experiment can be repeated thrice requiring 150 mice (50 mice×3). In addition, maximal orthotopic implantation rate can be achieved using in vivo passaged MB49 tumor cells. Typical flank subcutaneous (SQ) implantation rate of in vitro cultured MB49 cells is approximately 60-80% (6 out of 8 mice) and, therefore, 8 mice can be implanted with MB49 SQ to provide the 6 tumor-bearing mice required to ensure sufficient viable cells for the experiments. 8 mice×3 individual experiments=24 mice. Overall, 174 mice (150 experimental+24 donor) can be used for the proposed experiment.

The Table 3 experimental set-up using $MB49^{LE}$, $MB49^{LE}$ stably-expressing EGFRWT and $MB49^{LE}$ stably-expressing EGFRWT and Her2 for tumor generation can be used. These experiments can require at least 522 mice (3×174). Statistical analysis can be performed using two-way ANOVA.

There is evidence that intravesical instillation with EGF-toxin can reduce MB49-induced bladder tumors (leading to a total bladder weight close to tumor-free specimens) as compared to placebo (see FIG. 4E).

Example 5

Safety and antitumor-activity of EGF-toxin treatment in dogs with spontaneous bladder cancer: Entry criteria can include histopathologic diagnosis of TCC confined to the bladder (from cystoscopic biopsies), failure of any prior therapy, and expected survival of ≥6 weeks. Dogs can live at home with their families except when treated and evaluated. Tumor staging (thoracic radiography, abdominal ultrasonography, detailed bladder mapping by standardized protocol (Chun et al., (1997) *J. Vet. Intern. Med.* 11: 279-283)) and health assessment (physical exam, CBC, serum biochemical profile, urinalysis) are performed and during treatment. CT scanning (at least 2 scans per dog) are used to confirm ultrasound measurements and change in tumor size.

Treatment consists of instillation of EGF-toxin (5 nM EGF-PA'+10 nM $LF_N$-DTA) (daily×5 days per cycle) delivered through a urinary catheter as previously described (Abbo et al., (2010) *J. Vet. Intern. Med.* 24:1124-1130). After the 1 h treatment period, the EGF-toxin is removed and the bladder flushed with sterile saline. Cystoscopy is repeated on the 5th day of treatment to obtain biopsies for correlative biological changes. Following an initial 5 day treatment cycle, changes in tumor volume is tracked by weekly ultrasound exams to determine when the peak reduction in tumor size occurs and if cancer growth resumes, when this occurs. The initial plan can be to deliver one 5-day cycle of EGF-toxin per month, but this interval can be adjusted to optimize antitumor effects. The EGF-toxin treatment can continue as long as the cancer is controlled and the treatment is well tolerated. Dogs experiencing complete remission can undergo monthly evaluation to detect recurrence.

Based on encouraging preliminary studies, the EGF-toxin can be expected to induce complete or partial (≥50%) reduction and to be well tolerated.

Example 6

To determine the effect of EGFR concentration and other factors on the mechanism of EGF-toxin interaction with and entry in bladder cancer cells: EGFR quickly dimerizes upon ligand binding to form [EGFR:EGF]-[EGFR:EGF] complexes (Roskoski R Jr. (2014) *Pharmacol. Res.* 79: 34-74); EGF-PA' binding will also induce the formation of [EGFR:EGF-PA']-[EGFR:EGF-PA'] dimers; however, these complexes will have additional and unique properties, as shown in FIGS. 5A-5C. Specifically, resulting EGF-toxin heptamers contain some (or many) of these dimers, and each of them can participate in two heptamers giving rise to concatenated complexes (see FIG. 5C).

While not wishing to be bound by any one theory, as opposed to single pore (SP), due to size the multi-heptameric (or multi-pore: MP) complexes will utilizes Macropinocytosis/dorsal ruffles (Orth et al., (2006) *Cancer Res.* 66: 3603-3610; Bryant et al., (2007) *J. Cell Sci.* 120: 1818-1828) rather than endocytosis as an uptake mechanism. It is known that EGF can induce this mechanism switch in a dose-dependent manner (Orth et al., (2006) *Cancer Res.* 66: 3603-3610; Bryant et al., (2007) *J. Cell Sci.* 120: 1818-1828), and it is likely that MP size will favor membrane engulfing internalization processes. Further, bladder cancer cells have been shown to use these uptake mechanisms (Redelman-Sidi et al., (2013) *Cancer Res.* 73: 1156-1167).

The model proposed in FIG. 4 predicts that factors affecting the formation of dimers and toxin oligomerization would impact the balance of SP to MP complexes. Specifically, levels of EGFR (and Her2) and EGF-PA' (vs. other ligand; e.g., EGF) (FIGS. 5B-5D): the higher the concentration EGFR and EGF-PA', the higher the amount of pore bridging [EGFR:EGF-PA']-[EGFR:EGF-PA'] dimers. In contrast, the higher the levels of Her2, the higher the proportion of [EGFR:EGF-PA']-Her2 dimers unable to bridge pores (Her2 is unable to bind ligand, FIG. 5D). Endogenous EGF or HB-EGF (known to be present in urine and cells from patients) will also compete off the formation of heptamer-bridging dimers by forming [EGFR:EGF-PA']-[EGFR:EGF] or just [EGFR:EGF]-[EGFR:EGF] dimers (FIG. 5D).

Another factor that can affect the SP/MP complexes balance is the oligomer assembly versus uptake kinetics. It is known that EGF-bound EGFR dimers are quickly internalized, and the faster [EGFR:EGF-PA'] complexes are removed from the cell surface, the lower the proportion of oligomers and higher order-oligomers in the cell. Nevertheless, the results indicate that even after incubation times as short as 3 min, toxin oligomers are formed and able to mediate substantial cell death (FIG. 2C). Although these observations also reflect high toxin efficacy and are dependent of the levels of receptor and ligand, they indicate that that oligomer assembly is a fast process too.

Importantly, the factors mentioned above can be experimentally manipulated to favor/disfavor formation of MP complexes for testing model predictions. Determined is the presence of SP versus MP complexes as a function of receptor levels and variants and the impact of SP/MP proportion on EGF-toxin uptake mechanism and efficacy.

Using mouse bladder cancer MB49LE stably-transfected clones experimental conditions favoring or disfavoring MP complex assembly (see Table 4). The presence of SP and MP complexes under these conditions (Table 4) is directly assessed using high-resolution imaging techniques such as EM Tomography and super-resolution STORM microscopy. Using Table 4 conditions, the rate of internalization of SP versus MP complexes and presence of dorsal ruffles using live imaging with a spinning-disk confocal microscope can be investigated. The anti-tumor efficacy of MPs can be monitored by standard cell viability assays (FIGS. 2B-2D).

TABLE 4

Experimental conditions to control SP/MP complex proportion

| | MB49LE clone[a] | Treatment[b] | Readout | Expected Results |
|---|---|---|---|---|
| 1 | $EGFR^{WT}$-H | EGF-PA' | EM Tomography | Presence of MP complexes |
| 2 | $EGFR^{WT}$-ML | $LC_{100}$ (2 nM) | STORM-TIRFM | Condition: |
| 3 | $EGFR^{WT}$-ML/Her2-H | $LC_{50}$ (0.21 nM) ± | | 7, 9 > 6, 8 > others >> 5 |
| 4 | $EGFR^{K721M}$-H | EGF (2 nM) | | (100% SP complexes) |
| 5 | $EGFR^{Y246D}$-H | | | (i.e., higher EGFR levels + lower/ slower internalization rate → higher MP presence) |

TABLE 4-continued

| Experimental conditions to control SP/MP complex proportion | | | | | |
|---|---|---|---|---|---|
| | MB49LE clone[a] | Treatment[b] | | Readout | Expected Results |
| | | | | | Clone: #1, 4 > 2 > 3 >> 5 (100% SP complexes) EGF addition will decrease MP presence throughout. |
| 6 | $EGFR^{WT}$-H | EGF-PA' ($LC_{100}$) | ±Pitstop 2[c] (20 μM) | EM Tomography STORM-TIRFM | |
| 7 | $EGFR^{K721M}$-H | | | | |
| 8 | $EGFR^{WT}$-H | EGF-PA' ($LC_{100}$) | ±Amiloride[c] (25 μM) | EM Tomography STORM-TIRFM | |
| 9 | $EGFR^{K721M}$-H | | | | |
| 10 | $EGFR^{WT}$-H | EGF-PA' ($LC_{100}$) + $LF_N$ (10 nM) | | SDC | Rate of internalization and ruffle formation Single pore (#5-cond 11) > MP (#1-cond 10) |
| 11 | $EGFR^{Y246D}$-H | | | | |
| 12 | $EGFR^{WT}$-H | EGF-PA' ($LC_{50}$) | ±$LF_N$-DTA (10 nM) | MTT assay | Anti-tumor efficiency SP (5-cond 11) > MP (#1-cond 10) |
| 13 | $EGFR^{Y246D}$-H | | | | |

[a]All MB49LE clones express GFP-EGFR; [b]Cells are subjected to the stepwise approach (Table 1) with a final 10 min incubation at 37° C.; [c]Uptake inhibitors added 10 min before binding and maintained throughout the experiment. The potent and toxic amiloride analog EIPA will be used.

To impair/slow down endocytosis (conditions 6-9, Table IV), the following modification is applied to the stepwise approach of Table 1: Following serum-starvation, cells are pretreated with 20 μM Pitstop 2 for 5 min at 37° C. Washed with ice-cold saline once, added EGF-PA' in ice-cold saline+ Pitstop 2 and allowed to bind for 45 min at 4° C. Cells are washed with ice-cold saline, incubated at 37° C. in the presence of Pitstop 2 for 10 min, and processed for EM Tomography/STORM.

Uptake mechanism: Macropinocytosis/dorsal waves show sensitivity to specific chemical inhibitors such as Amiloride. This compound is assayed following the same experimental design than with Pitstop 2 (conditions 8, 9; Table 4). Direct observation of micropinocytosis/ruffle structures by SDC are performed using conditions 10, 11 (Table 4).

MPs may internalize at a slower rate and not all interconnected pores carry maximal $LF_N$-DTA load, leading to an inefficient use of EGF-PA'. Even if $LF_N$-DTA is loaded at maximal capacity they will lead to an "overkill" scenario with consequent inefficient use of the EGF-toxin system. Conditions 12, 13 in Table 4 compare the effect of MP formation versus a pure SP condition on the anti-tumor efficacy of the system.

Since EGF-PA' is HA-tagged in the linker region, anti-HA Fab antibody fragment conjugated to nano-gold and Alexa647 can be used for labeling pore complexes for EM.Tomography and STORM, respectively, using standard techniques. Fab fragments can be produced from the anti-HA monoclonal antibody HA.11 using the ImmunoPure Fab preparation kit (Pierce Biotechnology). The purified fragments can be labeled with AlexaFluor 647 Carboxylic acid, succinimidyl ester (Invitrogen) and sulfo-N-hydroxysuccinimide ester 1.4 nm Nanogold (Nanoprobes) following manufacturer instructions.

Example 7

In particular embodiments of the present invention, the receptor-binding activity of PA was ablated by mutating two residues of domain 4, and then fusing the C terminus of the mutated protein with heterologous receptor-binding proteins: human epidermal growth factor (EGF), HER2 affibody (ZHER2), or the receptor-binding domain of diphtheria toxin (DTR). The resulting fusion proteins mediated the entry of effector enzymes, and entry was dependent on the cellular receptors for EGF, ZHER2, and DTR.

In one example, two mutations in the domain 4 of the PA, N682A and D683A, were introduced into PA to ablate its native receptor-binding function (Rosovitz et al., 278 J. Biol. Chem. 30936 (2003)), and the mutated protein (mPA) was expressed in *E. coli* BL21 (DE3). SEQ ID NO: 10 provides the amino acid reference sequence for these mutants. The purified product failed to promote entry of LFwDTA into either CHO-KI cells or A431 cells at the highest concentration tested (10 nM), as measured by the inhibition of protein synthesis in the presence of LFwDTA. LFwDTA is a fusion between LPN, the N-terminal PA63-binding domain of LF, and DTA, the catalytic domain of diphtheria toxin. See PCT US2012/20731. The DTA moiety catalyzes the ADP-ribosylation of eukaryotic elongation factor-2 (eEF-2) within the cytosol, blocking protein synthesis and causing cell death. Collier & Cole, 164 Science 1179 (1969); Collier, 25 J. Mol. Biol. 83 (1967). The proteolytically activated form of PA, mPA63, was able to form SOS-resistant, high molecular weight aggregates, characteristic of pores, although pH dependence of pore formation was somewhat altered.

Then, the PA N682A/D683A double mutant (mPA), with its virtually ablated receptor-binding function, was fused to human EGF to the C-terminus of the mutated protein. Purified monomeric mPA-EGF was stable and ran slightly slower than native PA on SDS polyacrylamide gels, consistent with its higher molecular weight. Western blots showed that the product reacted with both anti-PA and anti-EGF antibodies. Also, it was also shown the mPA63-EGF fragment derived by trypsin treatment formed high molecular weight aggregates on SDS-PAGE similar to those seen with mPA63. PA 63 refers to amino acids 197-764 of SEQ ID NO: 9.

Although the complete anthrax PA amino acid sequence well known, it is provided herein for reference. The sequence includes a 29 amino acid signal peptide marked with bold and italicized:

MKKRKVLIPL MALSTILVSS TGNLEVIQAE VKQENRLLNE SESSSQGLLG YYFSDLNFQA PMVVTSSTTG DLSIPSSELE NIPSENQYFQ SAIWSGFIKV KKSDEYTFAT SADNHVTMWV DDQEVINKAS

NSNKIRLEKG RLYQIKIQYQ RENPTEKGLD FKLYVVTDSQN KKEVISSDNL QLPELKQKSS NSRKKRSTSA GPTVPDRDND GIPDSLEVEGYTVDVKNKRT FLSPWISNIH EKKGLTKYKS SPEKWSTASD PYSDFEKVTG RIDKNVSPEA RHPLVAA YPI VHVDMENIIL SKNEDQSTQN TDSQTRTISK NTSTSRTHTS EVHGNAEVHA SFFDIGGSVS AGFSNSNSST VAIDHSLSLA GERTWAETMG LNTADTARLN ANIRYVNTGT APIYNVLPTT SLVLGKNQTL ATIKAKENQL SQILAPNNYY PSKNLAPIAL NAQDDFSSTP ITMNYNQFLE LEKTKQLRLD TDQVYGNIAT YNFENGRVRV DTGSNWSEVL PQIQETTARI IFNGKDLNLV ERRIAAVNPS DPLETTKPDM TLKEALKIAF GFNEPNGNLQ YQGKDITEFD FNFDQQTSQN IKNQLAELNA TNIYTVLDKI KLNAKMNILI RDKRFHYDRN NIAVGADESV VKEAHREVIN SSTEGLLLNI DKDIRKILSG YIVEIEDTEG LKEVINDRYD MLNISSLRQD GKTFIDFKKY NDKLPLYISN PNYKVNVY AV TKENTIINPS ENGDTSTNGI KKILIFSKKG YEIG (SEQ ID NO: 9), Anthrax Protective antigen, with 29 as signal peptide; UniProtKB NO. P13423 (PAG_BACAN)

The following shows the anthrax PA amino acid sequence without the 29 amino acid signal peptide. The numbering references to the mutants throughout this specification relate to the sequence without the signal peptide. In the following, the N682A/D683A mutant is indicated with bold:

E VKQENRLLNE SESSSQGLLG YYFSDLNFQA PMVVTSSTTG DLSIPSSELE NIPSENQYFQ SAIWSGFIKV KKSDEYTFAT SADNHVTMWV DDQEVINKAS NSNKIRLEKG RLYQIKIQYQ RENPTEKGLD FKLYWTDSQN KKEVISSDNL QLPELKQKSS NSRKKRSTSA GPTVPDRDND GIPDSLEVEG YTVDVKNKRT FLSPWISNIH EKKGLTKYKS SPEKWSTASD PYSDFEKVTG RIDKNVSPEA RHPLVAA YPI VHVDMENIIL SKNEDQSTQN TDSQTRTISK NTSTSRTHTS EVHGNAEVHA SFFDIGGSVS AGFSNSNSST VAIDHSLSLA GERTWAETMG LNTADTARLN ANIRYVNTGT APIYNVLPTT SLVLGKNQTL ATIKAKENQL SQILAPNNYY PSKNLAPIAL NAQDDFSSTP ITMNYNQFLE LEKTKQLRLD TDQVYGNIAT YNFENGRVRV DTGSNWSEVL PQIQETTARI IFNGKDLNLV ERRIAAVNPS DPLETTKPDM TLKEALKIAF GFNEPNGNLQ YQGKDITEFD FNFDQQTSQN IKNQLAELNA TNIYTVLDKI KLNAKMNILI RDKRFHYDRN NIAVGADESV VKEAHREVIN SSTEGLLLNI DKDIRKILSG YIVEIEDTEG LKEVINDRYD MLNISSLRQD GKTFIDFKKY NDKLPLYISN PNYKVNVY AV TKENTIINPS ENGDTSTNGI KKILIFSKKG YEIG (SEQ ID NO: 10).

A431 cells, which express high levels of the EGF receptor (Lin et al., 224 Science 843 (1984); Ullrich et al., 309 Nature 418 (1984)), were killed by LFwDTA (EC50~10 pM) in the presence of mPA-EGF, whereas CHO-KI cells, which do not express the EGF receptor, were not killed. Wild-type PA also mediated the inhibition of protein synthesis in A43I cells, but a higher concentration of LFwDTA (EC50~100 pM) was needed, suggesting that these cells express a low level of ANTXRI, ANTXR2, or both. The translocation-deficient PA mutant, PAF427H (Krantz, 309 Science 777 (2005)), did not mediate killing on either A43I or CHO-KI cells.

If the entry of LFwDTA into A431 cells mediated by mPA-EGF was dependent on binding to the EGF receptor, then addition of free EGF should compete for binding and block toxicity. A 50-fold excess of EGF completely protected the cells from the cytotoxic effects of LFwDTA, whereas the same concentration of the PA-binding VWA domain of ANTXR2 had no effect. In contrast, cytotoxicity mediated by wild-type PA on A431 cells was ablated by the ANTXR2 domain, but was not inhibited to a significant degree by EGF.

The ability the mPA-EGF to translocate LF and EF, the native effector moieties of anthrax toxin, into A431 cells was also demonstrated in an exemplary system. LF inactivates mitogen-activated protein kinase kinases (MEKs) by cleaving near their N-termini (Duesbery et al., 1998; Vitale et al., 1998), and LF entry was characterized by Western blotting of cell lysates with an anti-MEKI antibody after incubating cells with LF plus PA or a variant thereof. MEKI was cleaved completely with LF in combination with PA or mPA-EGF, but not in combination with the translocation-deficient mutant PA F427H. Entry of EF was measured using an enzyme-linked competition assay to determine the intracellular level of cyclic AMP (cAMP) and with mPA-EGF as the translocation vehicle observed a 400-fold elevation of cAMP. This level was ~100× higher than that with WT PA, and the level observed with mPA or PAF427H was at background. The strong elevation observed with mPA-EGF was likely due in part to the high level of EGFR on the A431 cells.

The following mutations in PA are known to reduce toxicity by reducing cell binding, and can thus be used alone or in combination to ablate PA receptor binding.

| MUTATION LOCATION IN SEQ ID NO: 9 | Effect on receptor binding |
| --- | --- |
| 686 | N→A: Decrease in cell binding |
| 710 | Y→A: Decrease in cell binding |
| 711 | N→A: Decrease in cell binding |
| 712 | D→A: Decrease in cell binding |
| 715 | P→A: Decrease in cell binding |
| 716 | L→A: Decrease in cell binding |
| 718 | I→A: Decrease in cell binding |

In addition to LPN, analogues of bacterial toxins such as diphtheria toxin and cholera toxin can be used to deliver the therapeutic proteins. Thus, in one embodiment, the invention provides a method of treating a subject by contacting cells of the subject either in vivo or ex vivo with a composition comprising a fusion molecule comprising the component A or a surrogate A component attached to the therapeutic moiety. See PCT/US2012/20731. In another example, the 150-residue receptor-binding domain of diphtheria toxin (DTR) was fused to the C-terminus of mPA. The purified mPA-DTR fusion reacted with both anti-PA and anti-diphtheria toxin antibodies and retained the ability to oligomerize and form pores, and to bind and translocate cargo LFN-DTA in a planar bilayer system. The mPA-DTR variant delivered LFN-DTA into CHOKI cells, inhibiting protein synthesis, and soluble DTR competitively blocked this inhibition.

Generation of PA Expression Plasmids

One can construct the expression plasmids with any known sequences for the toxins according to routine methods and following, e.g., the principles used to make the below-described exemplary expression plasmid. In our examples we made the two PA chimeras used in this work: PAN682AD683A-EGF (mPA-EGF) and PAN682AD683A-DTR (mPA-DTR) were created by overlap extension PCR using a previously generated PAN682AD683A (mPA) gene coding sequence. In both cases the first PCR step consisted of two reactions (a) using a forward primer (PAFor-GATTTAGTAATTCGAATTCAAGTACGG) (SEQ ID NO:2), plus either PARevEGF (CATTCAGAGTCGCTGTTTGGT- TGCGTTTTATG) (SEQ ID NO:3), or PARevDTR (GTTTTATGCCCCGGAGATCCTATCTCATAGCC) (SEQ ID NO:4) reverse primers, which contained the EGF and DTR overlapping regions, respectively; and (b) using forward and reverse primers to amplify the EGF (EGFFor-CATAAAACGCAACCAAACAGCGACTATGAATG) (SEQ ID NO:5) and (EGFRev-GGTGGTGCTCGAGTCAACGGAGCTCCCACCATTTC) (SEQ ID NO:6) and DTR (DTRFor-GGCTATGAGATAGGATCTCCGGGGCATAAAAC) (SEQ ID NO:7) and (DTRRev-GTGGTGGTGGTGGTGCTCGAGTCAGCTTTTGATTTC) (SEQ ID NO:8) sequences. The PCR-generated DNA fragments were then subjected to a second PCR step using forward primer PAFor in combination with either the EGFRev or DTRRev primer, for PA-EGF and PA-DTR, to stitch and amplify the two fragments together. In both cases the full-length PCR products encoded EcoRI and XhoI restriction sites, in the forward and reverse primers, respectively. The PCR products were restriction digested and cloned into the pet22b expression vector following standard protocols. Each clone also coded for an 8-residue linker (SPGHKTQP, SEQ ID NO: 1) between PA and either EGF or DTR, which is part of the natural linker between the transmembrane and receptor-binding domains of diphtheria toxin.

Oligonucleotides were from Integrated DNA Technologies (Coralville, Iowa). Sigma-Aldrich (St. Louis, Mo.) supplied all chemicals unless noted otherwise. A synthetic human EGF gene, adjusted for *E. coli* expression, was a generous gift from Prof. E. Joop van Zoelen (Department of Cell Biology and Applied Biology, Heijendaalseweg, Nijmegen). Soluble EGF was from ProSpec-Tany Technogene Ltd (East Brunswick, N.J.).

Protein Expression and Purification

Recombinant wild-type PA (WT PA), PAF427H, mPA, mPA-EGF, and mPA-DTR were overexpressed in the periplasm of the BL21 (DE3) *E. coli* strain (Invitrogen, Carlsbad, Calif.). The resulting bacterial pellets were lysed and purified as described (Miller et al., 1999). Oligomeric prepares of WT PA and the various PA variants were produced by limited trypsin digestion at a final trypsin:PA ratio of 1:1000 (wt:wt) for 30 min at RT. The nicked proteins were subjected to anion-exchange chromatography, resulting in the separation of PA63 and PA20 fragments. PA63 spontaneously oligomerized to form porepore.

Purified mPA-EGF and mPA-DTR fusions were characterized by Western blot analysis. PA83 variants along with WT PA were subjected to SDS-PAGE and transferred to a polyvinylidene difluoride membrane (PVDF; Invitrogen, Carlsbad, Calif.). The membranes were blocked with Tris-buffered saline, pH 7.4, containing 2% BSA and hybridized with either mouse anti-PA (1:4000; cat. no. MAB8082; Millipore, Billerica, Mass.), rabbit anti-EGF (1:50000; cat. no. Ab9695; Abeam Cambridge, Mass.), or rabbit anti-DT antibodies (1:20000; cat. no. Ab53828; Abeam). Primary antibodies were detected with either goat anti-rabbit IgG (1:20000; Santa Cruz Biotechnology, Inc, Santa Cruz, Calif., cat. no. sc-2004) or rabbit anti-mouse IgG conjugated to HRP (1:10000; Santa Cruz, cat. no. sc-358914) with enhanced chemiluminescence (ECL) reagents (Pierce, Rockford, Ill.).

LF, EF, DTR, and LFwDTA were expressed in BL21 (DE3) *E. coli* (Invitrogen), under induction with 1 mM isopropyl-D-1-thiogalactopyranoside (IPTG) for 4 hours, using the Champion pet-SUMO expression system (Invitrogen). Cell pellets were lysed by sonication in lysis buffer (20 mM Tris-HCl pH 8.0, 150 mM NaCl, 10 mM imidazole, 10 mg lysozyme, 2 mg DNAase I, supplemented with a complete Roche protease inhibitor tablet). Following sonication, the lysates were cleared by centrifugation and loaded onto a 3 ml bed volume of Ni-NTA agarose (Qiagen, Valencia, Calif.). The resin was washed with 15 column volumes of wash buffer (20 mM Tris-HCl pH 8.0, 150 mM NaCl, 20 mM imidazole) and eluted with the same buffer supplemented with 250 mM imidazole. The resulting purified protein was exchanged into 20 mM Tris-HCl, pH 8.0, 150 mM NaCl, and cleaved with SUMO protease (Invitrogen) overnight at 4° C. Uncleaved His-SUMO fusion and SUMO protease were removed by a second round of Ni-NTA chromatography, in which the flow-thru contained the cleaved product of interest.

Cell Culture

The CHO-KI cell line was from the American Type Culture Collection (cat no. CCL-61, Manassas, Va.). Cells were maintained in Ham's F-12 medium supplemented with 10% fetal bovine serum (FBS), 500 units/ml penicillin G and 500 units/ml streptomycin sulfate (Life Technologies, Inc., Carlsbad, Calif.). The A431 cell line, also from the American Type Culture Collection (cat no. CCL-1555) was grown in Dulbecco's Modified Eagle's Medium, with 10% PBS, 500 units/ml penicillin G, 500 units/ml streptomycin sulfate, and 1 mM sodium pyruvate (American Type Culture Collection).

We claim:

1. A method of reducing an epidermal growth factor receptor (EGFR)-expressing bladder cancer tumor on the internal surface of the bladder of an animal or human patient, said method comprising reducing a population of EGFR-expressing cancer cells of the bladder cancer tumor by:

(a) delivering a dose of a therapeutic composition specifically targeting EGFR-expressing cancer cells to the lumen of the bladder of the patient having an EGFR-expressing bladder cancer tumor on the internal surface of the bladder, wherein the therapeutic composition comprises:

(i) a first fusion protein capable of specifically binding to an EGFR on the surface of a bladder cancer cell, wherein the first fusion protein comprises an epidermal growth factor (EGF) polypeptide conjugated to mutant anthrax Protective Antigen (PA') polypeptide PA' unable to selectively bind to an anthrax receptor, wherein the mutant anthrax Protective Antigen (PA') polypeptide comprises the mutations N682A and D683A, or at least one mutation selected from the group consisting of N686A, Y710A, N711A, D712A, P715A, L716A, and I718A, wherein the amino acid positions are numbered as in SEQ ID NO: 10;

(ii) a second fusion protein comprising an anthrax Lethal Factor N-terminus (LFN) conjugated to a Diphtheria Toxin A (DTA) catalytic domain; and (iii) a pharmaceutically acceptable carrier;

(b) determining the reduction in volume of the bladder cancer tumor compared to the volume of the bladder cancer tumor before delivering the therapeutic composition; and (c) adjusting the dose of the therapeutic composition by repeating steps (a)-(b) to reduce the volume of the bladder cancer tumor, when compared to the volume of the bladder cancer tumor before delivering the therapeutic composition, from about 30% to 100%.

* * * * *